(12) United States Patent
Peddada

(10) Patent No.: US 9,361,468 B2
(45) Date of Patent: Jun. 7, 2016

(54) METHOD AND SYSTEM FOR GRANTING ACCESS TO SECURE DATA

(71) Applicant: salesforce.com, inc., San Francisco, CA (US)

(72) Inventor: Prasad Peddada, Alameda, CA (US)

(73) Assignee: salesforce.com, inc., San Francisco, CA (US)

( * ) Notice: Subject to any disclaimer, the term of this patent is extended or adjusted under 35 U.S.C. 154(b) by 290 days.

(21) Appl. No.: 13/781,139

(22) Filed: Feb. 28, 2013

(65) Prior Publication Data

US 2013/0276142 A1 Oct. 17, 2013

Related U.S. Application Data

(60) Provisional application No. 61/625,198, filed on Apr. 17, 2012, provisional application No. 61/693,006, filed on Sep. 11, 2012.

(51) Int. Cl.
G06F 7/04 (2006.01)
G06F 17/30 (2006.01)
H04N 7/16 (2011.01)
G06F 21/62 (2013.01)
G06F 9/44 (2006.01)
H04L 29/06 (2006.01)
G06Q 30/02 (2012.01)
H04M 3/51 (2006.01)
G06F 19/00 (2011.01)
G06F 21/44 (2013.01)

(52) U.S. Cl.
CPC .............. *G06F 21/62* (2013.01); *G06F 9/4445* (2013.01); *G06F 21/6218* (2013.01); *G06F 19/327* (2013.01); *G06F 21/44* (2013.01); *G06Q 30/02* (2013.01); *H04L 63/0876* (2013.01); *H04M 3/51* (2013.01)

(58) Field of Classification Search
CPC ... G06F 21/62; G06F 21/6218; G06F 19/327; G06Q 30/02
USPC ........................ 726/21, 26–28; 705/26, 26.43
See application file for complete search history.

(56) References Cited

U.S. PATENT DOCUMENTS

| | | |
|---|---|---|
| 5,577,188 A | 11/1996 | Zhu |
| 5,608,872 A | 3/1997 | Schwartz |
| 5,649,104 A | 7/1997 | Carleton |
| 5,715,450 A | 2/1998 | Ambrose et al. |
| 5,761,419 A | 6/1998 | Schwartz |
| 5,819,038 A | 10/1998 | Carleton |
| 5,821,937 A | 10/1998 | Tonelli et al. |
| 5,831,610 A | 11/1998 | Tonelli et al. |
| 5,873,096 A | 2/1999 | Lim et al. |
| 5,918,159 A | 6/1999 | Fomukong et al. |
| 5,963,953 A | 10/1999 | Cram et al. |
| 6,092,083 A | 7/2000 | Brodersen et al. |
| 6,161,149 A | 12/2000 | Achacoso et al. |
| 6,169,534 B1 | 1/2001 | Raffel et al. |

(Continued)

Primary Examiner — Jayesh Jhaveri
(74) Attorney, Agent, or Firm — Dergosits & Noah LLP; Todd A. Noah

(57) ABSTRACT

Techniques described herein can be implemented as one or a combination of methods, systems or processor executed code to form embodiments capable of improved protection of data or other computing resources based at least in part upon limiting access to a select number of delegates. Limited access to cloud data based on customer selected or other criterion, reducing the possibility of security exposures and/or improving privacy is provided for.

21 Claims, 14 Drawing Sheets

(56) References Cited

U.S. PATENT DOCUMENTS

| | | |
|---|---|---|
| 6,178,425 B1 | 1/2001 | Brodersen et al. |
| 6,189,011 B1 | 2/2001 | Lim et al. |
| 6,216,135 B1 | 4/2001 | Brodersen et al. |
| 6,233,617 B1 | 5/2001 | Rothwein et al. |
| 6,266,669 B1 | 7/2001 | Brodersen et al. |
| 6,295,530 B1 | 9/2001 | Ritchie et al. |
| 6,324,568 B1 | 11/2001 | Diec |
| 6,324,693 B1 | 11/2001 | Brodersen et al. |
| 6,336,137 B1 | 1/2002 | Lee et al. |
| D454,139 S | 3/2002 | Feldcamp et al. |
| 6,367,077 B1 | 4/2002 | Brodersen et al. |
| 6,393,605 B1 | 5/2002 | Loomans |
| 6,405,220 B1 | 6/2002 | Brodersen et al. |
| 6,434,550 B1 | 8/2002 | Warner et al. |
| 6,446,089 B1 | 9/2002 | Brodersen et al. |
| 6,535,909 B1 | 3/2003 | Rust |
| 6,549,908 B1 | 4/2003 | Loomans |
| 6,553,563 B2 | 4/2003 | Ambrose et al. |
| 6,560,461 B1 | 5/2003 | Fomukong et al. |
| 6,574,635 B2 | 6/2003 | Stauber et al. |
| 6,577,726 B1 | 6/2003 | Huang et al. |
| 6,601,087 B1 | 7/2003 | Zhu |
| 6,604,117 B2 | 8/2003 | Lim et al. |
| 6,604,128 B2 | 8/2003 | Diec |
| 6,609,150 B2 | 8/2003 | Lee et al. |
| 6,621,834 B1 | 9/2003 | Scherpbier |
| 6,654,032 B1 | 11/2003 | Zhu |
| 6,665,648 B2 | 12/2003 | Brodersen et al. |
| 6,665,655 B1 | 12/2003 | Warner et al. |
| 6,684,438 B2 | 2/2004 | Brodersen et al. |
| 6,711,565 B1 | 3/2004 | Subramaniam et al. |
| 6,724,399 B1 | 4/2004 | Katchour et al. |
| 6,728,702 B1 | 4/2004 | Subramaniam et al. |
| 6,728,960 B1 | 4/2004 | Loomans |
| 6,732,095 B1 | 5/2004 | Warshavsky et al. |
| 6,732,100 B1 | 5/2004 | Brodersen et al. |
| 6,732,111 B2 | 5/2004 | Brodersen et al. |
| 6,754,681 B2 | 6/2004 | Brodersen et al. |
| 6,763,351 B1 | 7/2004 | Subramaniam et al. |
| 6,763,501 B1 | 7/2004 | Zhu |
| 6,768,904 B2 | 7/2004 | Kim |
| 6,772,229 B1 | 8/2004 | Achacoso et al. |
| 6,782,383 B2 | 8/2004 | Subramaniam et al. |
| 6,804,330 B1 | 10/2004 | Jones et al. |
| 6,826,565 B2 | 11/2004 | Ritchie et al. |
| 6,826,582 B1 | 11/2004 | Chatterjee et al. |
| 6,826,745 B2 | 11/2004 | Coker |
| 6,829,655 B1 | 12/2004 | Huang et al. |
| 6,842,748 B1 | 1/2005 | Warner et al. |
| 6,850,895 B2 | 2/2005 | Brodersen et al. |
| 6,850,949 B2 | 2/2005 | Warner et al. |
| 7,062,502 B1 | 6/2006 | Kesler |
| 7,340,411 B2 | 3/2008 | Cook |
| 7,356,482 B2 | 4/2008 | Frankland et al. |
| 7,401,094 B1 | 7/2008 | Kesler |
| 7,620,655 B2 | 11/2009 | Larsson |
| 7,698,160 B2 | 4/2010 | Beaven et al. |
| 7,779,475 B2 | 8/2010 | Jakobson et al. |
| 7,851,004 B2 | 12/2010 | Hirao et al. |
| 8,010,663 B2 | 8/2011 | Firminger et al. |
| 8,014,943 B2 | 9/2011 | Jakobson |
| 8,015,495 B2 | 9/2011 | Achacoso et al. |
| 8,032,297 B2 | 10/2011 | Jakobson |
| 8,082,301 B2 | 12/2011 | Ahlgren et al. |
| 8,095,413 B1 | 1/2012 | Beaven et al. |
| 8,095,594 B2 | 1/2012 | Beaven et al. |
| 8,185,550 B1 * | 5/2012 | Eichler et al. ............... 707/783 |
| 8,209,308 B2 | 6/2012 | Jakobson et al. |
| 8,275,836 B2 | 9/2012 | Beaven et al. |
| 8,484,111 B2 | 7/2013 | Frankland et al. |
| 8,490,025 B2 | 7/2013 | Jakobson et al. |
| 8,504,945 B2 | 8/2013 | Jakobson et al. |
| 8,510,664 B2 | 8/2013 | Rueben et al. |
| 8,566,301 B2 | 10/2013 | Rueben et al. |
| 8,646,103 B2 | 2/2014 | Jakobson et al. |
| 8,826,420 B2 * | 9/2014 | Boss et al. ..................... 726/21 |
| 8,850,525 B1 * | 9/2014 | Wilkinson ............ G06F 9/4445 709/203 |
| 2001/0044791 A1 | 11/2001 | Richter et al. |
| 2002/0072951 A1 | 6/2002 | Lee et al. |
| 2002/0082892 A1 | 6/2002 | Raffel |
| 2002/0129352 A1 | 9/2002 | Brodersen et al. |
| 2002/0140731 A1 | 10/2002 | Subramaniam et al. |
| 2002/0143997 A1 | 10/2002 | Huang et al. |
| 2002/0162090 A1 | 10/2002 | Parnell et al. |
| 2002/0165742 A1 | 11/2002 | Robbins |
| 2003/0004971 A1 | 1/2003 | Gong |
| 2003/0018705 A1 | 1/2003 | Chen et al. |
| 2003/0018830 A1 | 1/2003 | Chen et al. |
| 2003/0066031 A1 | 4/2003 | Laane et al. |
| 2003/0066032 A1 | 4/2003 | Ramachandran et al. |
| 2003/0069936 A1 | 4/2003 | Warner et al. |
| 2003/0070000 A1 | 4/2003 | Coker et al. |
| 2003/0070004 A1 | 4/2003 | Mukundan et al. |
| 2003/0070005 A1 | 4/2003 | Mukundan et al. |
| 2003/0074418 A1 | 4/2003 | Coker et al. |
| 2003/0120675 A1 | 6/2003 | Stauber et al. |
| 2003/0151633 A1 | 8/2003 | George et al. |
| 2003/0159136 A1 | 8/2003 | Huang et al. |
| 2003/0187921 A1 | 10/2003 | Diec et al. |
| 2003/0189600 A1 | 10/2003 | Gune et al. |
| 2003/0204427 A1 | 10/2003 | Gune et al. |
| 2003/0206192 A1 | 11/2003 | Chen et al. |
| 2004/0001092 A1 | 1/2004 | Rothwein et al. |
| 2004/0015981 A1 | 1/2004 | Coker et al. |
| 2004/0027388 A1 | 2/2004 | Berg et al. |
| 2004/0068421 A1 * | 4/2004 | Drapeau ............ G06F 19/3418 705/2 |
| 2004/0128001 A1 | 7/2004 | Levin et al. |
| 2004/0186860 A1 | 9/2004 | Lee et al. |
| 2004/0193510 A1 | 9/2004 | Catahan et al. |
| 2004/0199489 A1 | 10/2004 | Barnes-Leon et al. |
| 2004/0199536 A1 | 10/2004 | Barnes Leon et al. |
| 2004/0249854 A1 | 12/2004 | Barnes-Leon et al. |
| 2004/0260534 A1 | 12/2004 | Pak et al. |
| 2004/0260659 A1 | 12/2004 | Chan et al. |
| 2004/0268299 A1 | 12/2004 | Lei et al. |
| 2005/0050555 A1 | 3/2005 | Exley et al. |
| 2005/0091098 A1 | 4/2005 | Brodersen et al. |
| 2006/0031144 A1 * | 2/2006 | Todd ............................... 705/26 |
| 2006/0053035 A1 * | 3/2006 | Eisenberg ............ G06Q 50/22 705/2 |
| 2009/0063415 A1 | 3/2009 | Chatfield et al. |
| 2009/0100342 A1 | 4/2009 | Jakobson |
| 2009/0177744 A1 | 7/2009 | Marlow et al. |
| 2010/0100412 A1 * | 4/2010 | Cases ................... G06Q 10/06 705/7.27 |
| 2012/0021721 A1 * | 1/2012 | Reed et al. ................... 455/411 |
| 2012/0233137 A1 | 9/2012 | Jakobson et al. |
| 2012/0320905 A1 * | 12/2012 | Ilagan ........................... 370/352 |
| 2013/0218948 A1 | 8/2013 | Jakobson |
| 2013/0218949 A1 | 8/2013 | Jakobson |
| 2013/0218966 A1 | 8/2013 | Jakobson |
| 2014/0359537 A1 | 12/2014 | Jackobson et al. |
| 2015/0006289 A1 | 1/2015 | Jakobson et al. |
| 2015/0095162 A1 | 4/2015 | Jakobson et al. |
| 2015/0172563 A1 | 6/2015 | Jakobson et al. |

* cited by examiner

METHOD AND SYSTEM FOR GRANTING ACCESS TO SECURE DATA

PRIORITY

This application claims priority to commonly assigned U.S. Provisional Patent Application No. 61/625,198 entitled "Debugging Customer Issues without Accessing Customer Data in an On-demand Services Environment" filed Apr. 17, 2012, and U.S. Provisional Patent Application No. 61/693,006, entitled "Methods and Systems for Granting Access to Secure Data" filed Sep. 11, 2012, all of which are hereby incorporated by reference in their entirety and for all purposes.

TECHNICAL FIELD

Described herein are embodiments realized as methods, computer systems, software and networks configured to support applications executing on behalf of users accessing them as services. More particularly, specific embodiments relate to methods and systems for selecting delegates to have access to private customer data in conjunction with issue resolution or other purposes.

BACKGROUND

Modern software development is evolving away from the client-server model toward network-based processing systems that provide access to data and services via the Internet or other networks. In contrast to traditional systems that host networked applications on dedicated server hardware, a "cloud" computing model allows applications to be provided over the network "as a service" supplied by an infrastructure provider. The infrastructure provider typically abstracts underlying hardware and other resources used to deliver an application so that the customer no longer needs to operate and support dedicated server hardware. The cloud computing model can often provide substantial cost savings to the customer over the life of the application because the customer no longer needs to provide dedicated network infrastructure, electrical and temperature controls, physical security and other logistics in support of dedicated server hardware. Cloud-based architectures have been developed to improve collaboration, integration, and community-based cooperation between customer entities without sacrificing data security. During operation, situations can arise in which data and/or other computing resources allocated to a customer need to be accessed by someone other than the customer (e.g., for maintenance).

Unfortunately, while conventional approaches can indeed grant to support users or administrators access to customer resources, there remains a need to provide customers and/or others with the ability to control the access granting process. Customers can, for instance, have special requirements that they would like to place upon those given access to the customer's resources in the cloud. By granting complete access to all support users, a conventional cloud environment makes customer resources unnecessarily available to greater numbers of users, contexts, confidentiality and/or other security risks, and/or other potentially disfavored scenarios. Therefore, what is needed is a remedy to this and other shortcomings of the traditional on line support access.

BRIEF DESCRIPTION OF THE DRAWINGS

A more complete understanding of the subject matter can be derived by referring to the detailed description and claims when considered in conjunction with the following figures, wherein like reference numbers refer to similar elements throughout the figures.

DETAILED DESCRIPTION

Figure 1A:
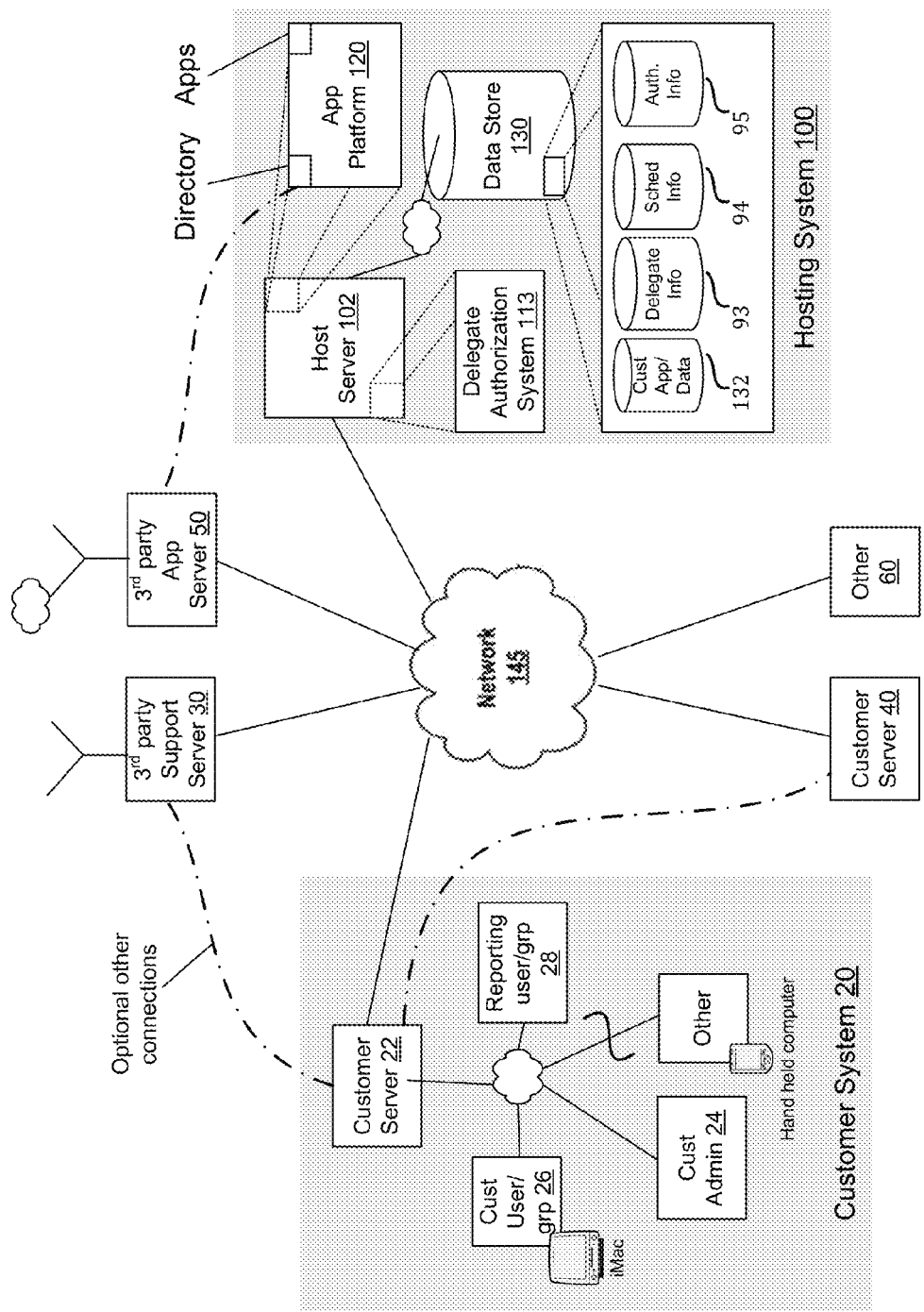
FIG. 1a is a block diagram of an exemplary hosted computing environment in which embodiments can be realized.

Techniques described herein can be implemented as one or a combination of methods, systems or processor executed code to form embodiments capable of improved protection of data or other computing resources based at least in part upon limiting access to select delegates. Embodiments can enable delegates to impersonate customer support and/or other personnel yet the activities of individual delegates can be tracked for accountability or other purposes.

An embodiment provides controlled access to cloud data based on customer selected as well as other criterion, reducing the possibility of security exposures.

An embodiment provides verifiable tracking of activities of delegates provided with permissions to log in as and/or otherwise impersonate a customer that granted authorization to the delegate.

An embodiment provides for adding potential delegates to a set of authorized delegate(s) based upon attributes corresponding to criterion for example, thereby granting access to delegates where such access was not otherwise provided to such users and/or groups of users.

An embodiment provides for filtering out potential delegates from further consideration for a particular request, thereby limiting access to a broader collection of users and/or groups of users, and/or some combination thereof.

One embodiment provides a computer-implemented method for selecting delegates to have access to private customer data. While also applicable to other scenarios in which delegate access might be desirable, a more specific embodiment provides for such selection in conjunction with issue resolution, for example, by cloud host, customer, third party and/or other personnel to which access might be delegated for providing for application, data, operational, transactional and/or other issue resolution, for example, in response to a request. A method can include receiving via a computing device an electronic format request on behalf of a customer. A method can include determining a set of potential delegates corresponding to the electronic format request. A method can include determining attributes corresponding to the set of potential delegates. A method can include determining one or more authorization filters. An authorization filter can include one or more authorization criterion corresponding to the customer. A method can include determining whether any one of the set of potential delegates can be authorized to access private customer data of the customer by applying an authorization filter to the attributes corresponding to the set of potential delegates to determine a set of authorized delegates. Authorized delegates can be selected based at least upon a correspondence between one or more of the attributes of the potential delegate(s) to one or more criterion. A method can include determining, from the set of authorized delegates, at least one delegate to be assigned to the electronic format request.

One embodiment provides a computer-implemented method for determining a number of candidates available to meet a criterion of interest. A method can include receiving a criterion of interest on behalf of a customer. A method can include determining a set of potential delegates corresponding to the criterion of interest. A method can include determining attributes corresponding to the set of potential delegates. A method can include determining at least one authorization filter. The at least one filter can include authorization criterion corresponding to the customer. A method can include determining whether any one of the set of potential delegates can be authorized to access private customer data of the customer by applying the at least one authorization filter to the attributes corresponding to the set of potential delegates to determine a set of authorized delegates, based at least in part on determining a correspondence between at least one of the attributes to the criterion of interest. A method can include determining, from the set of authorized delegates, a number of candidates available to meet the criterion of interest.

FIG. 1a is a block diagram of an exemplary hosted computing environment in which embodiments can be realized. As shown in FIG. 1a, a plurality of integral, non-integral and/or network elements, configurable into a more distributed or more integrated manner, comprise a hosted computing environment in which consumers can obtain computing resources as services from providers. For example, a customer system 20 (sometimes referred to as a services consumer, enterprise customer, tenant or "private cloud") can obtain hosted services by communicatively coupling with hosting system 100 (also called a cloud provider, "public cloud", or the like) via network 145. Further, customers can exchange data, applications and services with their customers 40 and with third party providers 30 via network 145 and/or optional other connections.

Individual configurations vary widely with the computing needs of the customer, but the example customer system 20 comprises a variety of communicatively coupled components deployable at the customer's location and/or elsewhere, including customer server 22, customer admin 24, customer users/user groups 26, reporting user groups 28 and others not shown in FIG. 1a for clarity.

Hosting systems that deliver computing services to the customer vary greatly, but hosting system 100 comprises data store 130 that provides storage of data for customers, hosting system provider and third parties, communicatively coupled with host server 102 that provides an application platform 120 for hosting applications of customers, hosting system provider and third parties, and provides security capabilities for determining access permission for customers, support users, and others controlled by delegate authorization system 113.

Delegate authorization system 113 provides for granting access to designated resources of hosting system 100 to customers and users with proper permissions; and in an exemplary embodiment, providing for customer contribution to definition and control of permissions governing which persons can respond to customer requests. Requests can be requests to perform a service, requests for support, audit requests, requests to perform labor under contract or otherwise, or other such types of requests.

An embodiment of delegate authorization system 113 provides for issuing an authorization to a delegate can include granting to the delegate access to private customer data and enabling the delegate to impersonate the customer generally, in all or more specific circumstances and/or with respect to all or a subset of the customer data (e.g., providing limited access privileges). Enabling the delegate to impersonate the customer can be achieved in part by combining permissions of the customer and the delegate. In some embodiments, activities of the delegate can be tracked.

An embodiment of delegate authorization system 113 provides for adding zero or more potential delegates to a set of authorized delegate(s) based upon attributes corresponding to criterion for example, thereby granting access to delegates where such access was not otherwise provided to such users and/or groups of users. In another embodiment, zero or more potential delegates can be filtered out from further consideration for a particular request, thereby limiting access to a broader collection of users and/or groups of users, and/or some combination thereof.

Figure 1B:
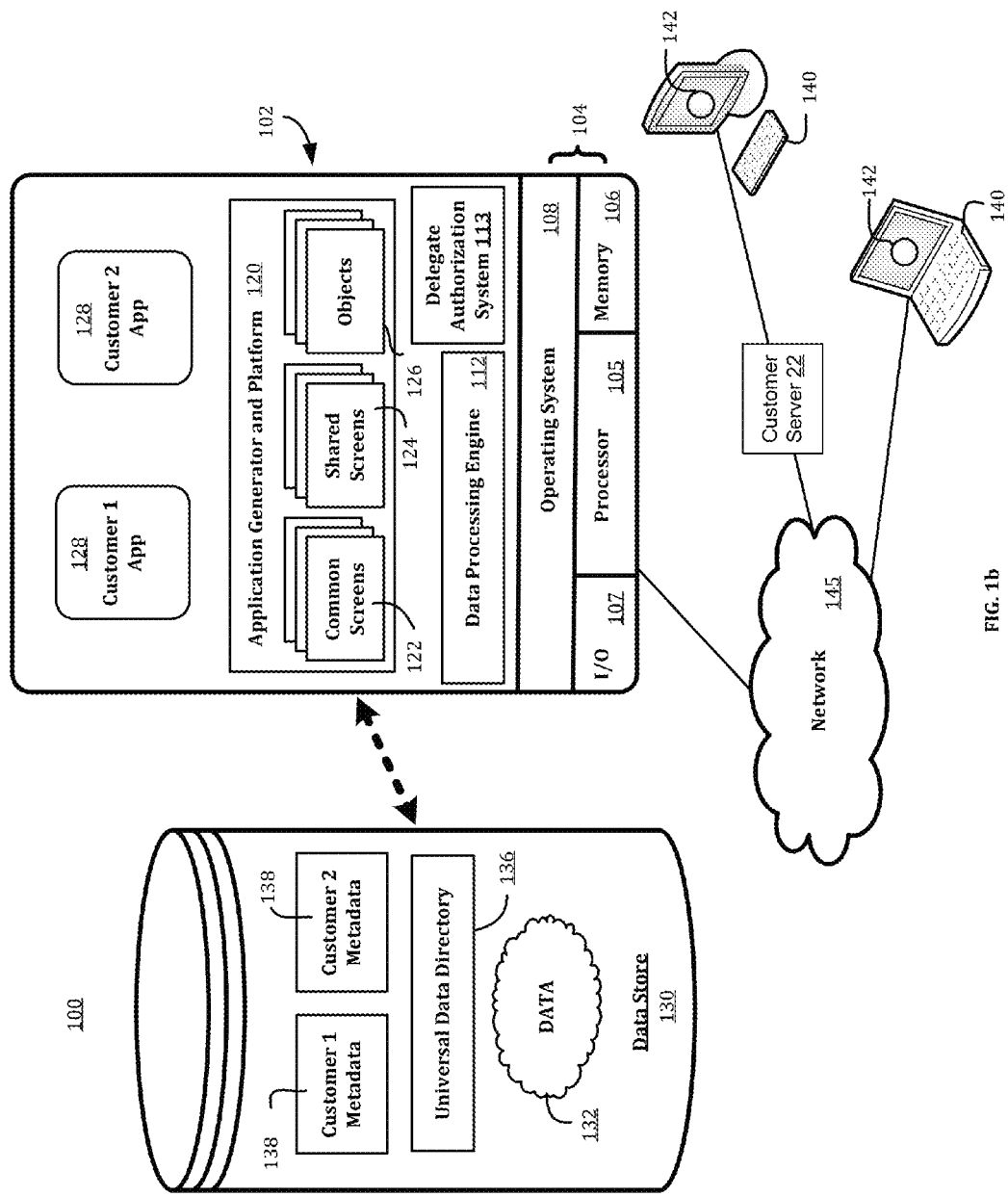
FIG. 1b is a block diagram of an exemplary hosting system embodiment in which customers request services and authorized parties are notified and gain access.

Turning now to FIG. 1b, an exemplary hosting system is illustrated in which customers request services and authorized parties are notified and gain access. System 100 suitably includes a server 102 that dynamically creates and supports virtual applications 128 based upon data 132 from a computing resource, data store 130, which can be shared. In some embodiments, data store 130 can be a common database or set of databases shared among different tenants, and in such case, it can be referred to as a multi-tenant database, however, multi-tenancy is not a requirement of data store 130. Data and services generated by the virtual applications 128 are provided via a network 145 to any number of client devices 140, as desired. Each virtual application 128 can be suitably generated at run-time using a common application platform 120 that securely provides access to the data 132 in the data store 130 for each of the various submitters subscribing to the system 100. In accordance with one example, the system 100 can implement one or more specific functions, such as for example a customer relationship management (CRM) system, an Enterprise resource planning (ERP) system, a Partner Relationship Management (PRM) system and/or any or a combination of these and/or other applications.

Some hosting system embodiments can employ multi-tenancy techniques, however multi-tenancy is not required. Generally speaking, multi-tenancy refers to techniques where a hardware and software platform simultaneously supports multiple user groups (also referred to as "organizations" or "tenants") from one or more common computational resources, such as a data storage element, server hardware, server image, systems architecture, database schema, custom objects and/or fields, other like computational elements, and/ or some combination thereof. For example, one type of multi-tenant data storage (referred to as a "multi-tenant database") can be created based upon a relational database, however embodiments can be realized using object oriented database, or other types of databases, or some combination thereof. For example, a "tenant" or an "organization" can be used to refer to a group of one or more users that shares access to a common subset of the data (i.e., one or more contiguous and/or non-contiguous portions) within the multi-tenant database. In this regard, each tenant includes one or more users and/or groups of users associated with, assigned to or otherwise belonging to that respective tenant. Tenants can represent customers, customer departments, business or legal organizations, and/or any other entities that maintain data for particular sets of users and/or groups of users within a common multi-tenant system.

In a multi-tenancy embodiment, multiple tenants can share access to the server 102 and the data store 130 however the particular data and services provided from the server 102 to each tenant or further, to tenant sub-groupings and/or super-groups thereof, other tenants, sub-groupings and/or super-groupings thereof, can be securely isolated from those provided to other tenants. Embodiments therefore enable different sets of users to share functionality without necessarily sharing any of the data 132 belonging to or otherwise associated with other tenants. Multi-tenant design choices can enable one or more advantages. For example, the multi-tenant platform operator can often make improvements to the platform based upon collective information from a broader tenant community. Additionally, because pluralities of users at different tenants can execute applications within a common processing space, access can be granted or denied to specific sets of data for any user within the multi-tenant platform, thereby improving collaboration and integration with respect to data managed by various applications, component services or combinations thereof.

The data store 130 can be realized using any type(s) of data repository and/or data storage technology capable of storing and managing the data 132 associated with any number of submitters. The data store 130 can be implemented using any type or combination of types of database server(s) for example. In various embodiments, the data store 130 shares processing hardware 104 with the server 102. In other embodiments, the data store 130 is implemented using separate physical and/or virtual database server hardware and/or storage hardware that communicate with the server 102 to perform the various functions described herein. Further, data store 130 can include database manager function implemented as software, firmware or acceptable combinations thereof.

In practice, the data 132 can be organized and formatted in any suitable manner to support the application platform 110. In various embodiments, the data 132 is suitably organized into a relatively small number of large data tables to maintain a semi-amorphous "heap"-type format. The data 132 can then be physically and/or virtually organized as needed for a particular virtual application 128 using data models, data schema, views or combinations thereof. In various embodiments, conventional data relationships can be established using any number of pivot tables 134 that establish indexing, uniqueness, relationships between entities, and/or other aspects of database organization as desired. Further data manipulation and report formatting is generally performed at run-time using a variety of metadata constructs. Metadata within a universal data directory (UDD) 136, for example, can be used to describe any number of forms, reports, workflows, user access privileges, business logic and other constructs shared by users at a tenant. In multi-tenant embodiments, tenant-specific formatting, functions and other constructs can be maintained as customer metadata 138 for any particular tenant, subset, sub-grouping and/or superset thereof, as desired. Rather than forcing the data 132 into an inflexible global structure that is common to all tenants and applications, the data store 130 can be organized to be relatively amorphous, with the pivot tables 134 and the metadata 138 providing additional structure on an as-needed basis. To that end, the application platform 110 suitably uses the pivot tables 134 and/or the metadata 138 to generate "virtual" components of the virtual applications 128 to logically obtain, process, and present the relatively amorphous data 132 from the data store 130.

The server 102 can be implemented using one or more actual and/or virtual computing systems that collectively provide the dynamic application generator 120 for generating the virtual applications 128. For example, the server 102 can be implemented using a cluster of actual and/or virtual servers operating in conjunction with each other, typically in association with conventional network communications, cluster management, load balancing and/or other features as appropriate. The server 102 can be implemented using any suitable conventional processing hardware 104, such as a processor 105, memory 106, input/output features 107 and the like. The input/output features 107 generally represent the interface(s) to networks (e.g., to the network 145, or any other local area, wide area or other network), mass storage, display devices, data entry devices and/or the like. The processor 105 can be implemented using any suitable processing system, such as one or more processors, controllers, microprocessors, micro-controllers, processing cores and/or other computing resources spread across any number of distributed or integrated systems, including any number of "cloud-based" or other virtual systems. The memory 106 represents any non-transitory short or long term storage or other computer-readable media capable of storing programming instructions for execution on the processor 105, including any sort of random access memory (RAM), read only memory (ROM), flash memory, magnetic or optical mass storage, and/or the like. The computer-executable programming instructions, when read and executed by the server 102 and/or processor 105, cause the server 102 and/or processor 105 to establish, generate, or otherwise facilitate the application generator 120 and/or virtual applications 128 and perform additional tasks, operations, functions, and processes therein. It should be noted that the memory 106 represents one suitable implementation of such computer-readable media, and alternatively or additionally, the server 102 could receive and cooperate with computer-readable media (not separately shown) that can be realized as a portable or mobile component or platform, e.g., a portable hard drive, a USB flash drive, an optical disc, or the like.

The application generator 120 can include any suitable software application or other data processing engine that generates the virtual applications 128 that provide data and/or services to the client devices 140. In a typical embodiment, the application generator 120 gains access to processing resources, communications interfaces and other features of the processing hardware 104 using any suitable conventional or proprietary operating system 108. While capable of being pre-compiled, the virtual applications 128 are typically generated at run-time in response to input received from the client devices 140, or alternatively generated from a combination of pre-compiled and run-time generated components. Each of the illustrated features can be implemented as a separate process or other module, and many equivalent embodiments can include different and/or additional features, components or other modules as desired.

The runtime application generator 120 dynamically builds and executes the virtual applications 128 in response to specific requests received from the client devices 140. The virtual applications 128 are typically constructed in accordance with the customer metadata 138, which describes the particular tables, reports, interfaces and/or other features of the particular application 128. In various embodiments, each virtual application 128 generates dynamic web content that can be served to a browser or other client program 142 associated with its client device 140, as appropriate.

In operation, developers can use the application generator 120 to create data-driven virtual applications 128 for the customers that they support. Such virtual applications 128 can make use of interface features such as tenant-specific, for example, screens 124, universal screens 122 or the like. Any number of tenant-specific and/or universal objects 126 also can be available for integration into virtual applications 128. The data 132 associated with each virtual application 128 is provided to the database 130, as appropriate, and stored until it is requested or is otherwise needed, along with the metadata 138 that describes the particular features (e.g., reports, tables, functions, etc.) of that particular virtual application 128. For example, a virtual application 128 can include a number of objects 126 accessible to users of a particular customer, for example, wherein for each object 126, information pertaining to its object type along with values for various fields associated with that respective object type are maintained as metadata 138 in the data store 130. In this regard, the object type can define the structure (e.g., the formatting, functions and other constructs) of each respective object 126 and the various fields associated therewith.

Again referring to FIG. 1b, the data and services provided by server 102 can be retrieved using any sort of personal computer, mobile telephone, tablet and/or substantially any other suitably network-enabled client device 140 on the network 145. In various embodiments, the client device 140 includes a display device, such as a monitor, screen, or another conventional electronic display capable of graphically presenting data and/or information retrieved from the data store 130. Typically, the user operates a conventional browser, other client program 142 or some combination thereof that is executed by the client device 140 to communicate with the server 102 via the network 145 and optionally customer server 22 using a networking protocol, such as the hypertext transport protocol (HTTP), Hypertext Transfer Protocol Secure (HTTPS) or the like. When using a stateless protocol such as HTTP or HTTPS, the user typically authenticates his or her identity to the server 102 to obtain a session identifier ("SessionID") that identifies the user in subsequent communications with the server 102 and/or such authentication can be conducted automatically (e.g., whereby the system receives and analyzes biometric and/or other authenticating information). When the authenticated user requests access to a virtual application 128, the application generator 120 suitably creates the application at run time based upon the metadata 138, as appropriate. As noted above, the virtual application 128 can contain Java, ActiveX, or other content that can be presented using conventional client software running on the client device 140; other embodiments can simply provide dynamic web or other content that can be presented and viewed by the user, as desired. Query generator 114 suitably obtains requested subsets of data 132 from the data store 130 as needed to populate the tables, reports or other features of the particular virtual application 128. As described in greater detail below, users can authorize delegates to access select portions of the user's data 132 in data store 130, applications 128 or combinations thereof using delegate authorization system 113 for providing application, data, operational, transactional and/or other issue resolution, for example, in response to a request.

Figure 2A:
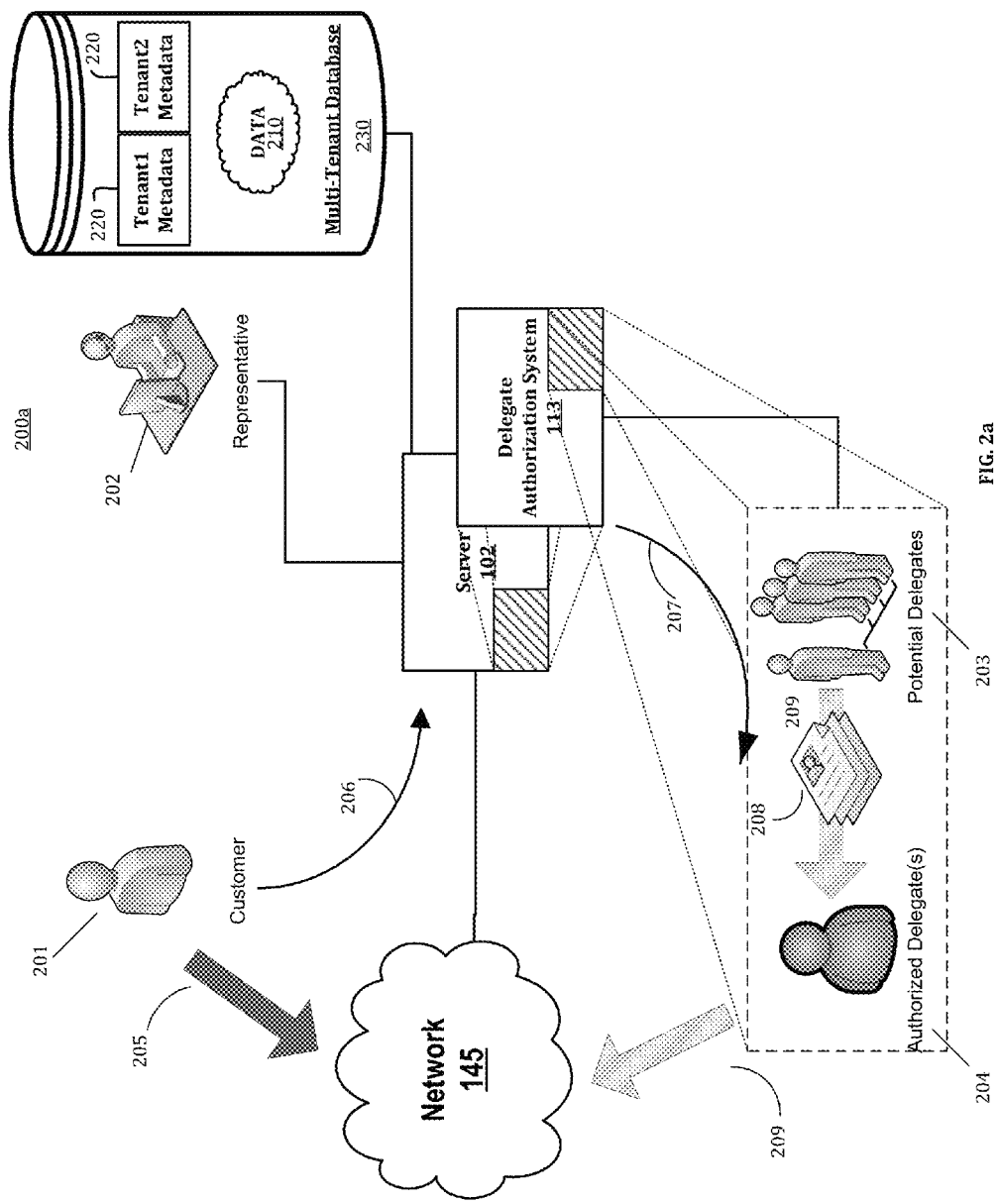
FIG. 2a is a flow diagram illustrating a hosting system embodiment that implements a multi-tenant database and in which the customer requests services and the authorized parties are notified and gain access.

FIG. 2a illustrates a further example of a system embodiment that utilizes a multi-tenant database (e.g., multi-tenant database system), and in which a user at a customer requests services and authorized parties are notified and gain access. Note that each of user 201, representative 202, potential delegates 203 and authorized delegate(s) 204, when communicating with system 200a, can communicate using a suitable client device, e.g., such as with client devices 140 of FIG. 1b, which are not shown in FIG. 2 for clarity sake. It will be appreciated that the directional arrows are not limiting and other, e.g., bi-directional, communication can also be conducted. For example, a customer 201, who can be experiencing an issue, contacts representative 202 for assistance. The issue might involve a service issue, an audit request, a request for contract labor to be performed or the like. The representative 202 can be human, machine based proxy for human intervention or suitable combination thereof. Contact between customer 201 and representative 202 can be via telephone and/or facilitated over a network or the like. In one application, the representative 202 is a support representative, for example, being contacted about a technical issue involving customer 201 attempting to access 205 (or otherwise work with) one or more cloud based computing resources of hosting system 100 of FIG. 1. Among other examples, the representative 202 can be a service representative, audit representative, contract labor representative or the like, being contacted by customer 201 to resolve some issue which requires access to computing resources of system 100 of FIG. 1. Customer 201 may, for example, be experiencing an issue while accessing one or more of multi-tenant database 230, data 210, or tenant metadata 220 via server 102 and network 145.

Customer 201 submits an electronic format request 206 via a computing device such as a computer, mobile telephone, tablet computer or the like, to obtain assistance. Electronic format request 206 can be a request expressed in electronic format by customer 201, a request communicated to an intermediary, such as representative 202, that converts the request into an electronic format, or a suitable combination thereof. Requests can include any type of electronic communication in which some requests of given type can be ascertained from the communication. Requests can be entered into an electronic device or determined automatically from an electronic communication by analysis that flags something in the electronic communication. Common electronic formats can include a form with issue entry selection, which can be a field to be filled in, a drop down menu and/or other type of indication, an email or text message, a transcription of a telephone call, and other types of electronic formats. In cases where processing the request requires analysis of more generic forms of communication, system 200a includes a model for analyzing communication such as speech recognition techniques, natural language processing, fuzzy logic, term recognition or search and/or combinations of these and other communications or other semantic analysis techniques, many of which are useful for analyzing communications to identify meaning. Once received, the request 206 can be processed by delegate authorization system 113 of server 102. In the event that processing the request includes giving permission to a delegate to access private data 210 or applications 128 or other computing resources of customer 201, authorization system 113 can determine one or more authorized delegate(s) 204 to be issued an authorization 207 enabling that delegate(s) 204 to access computing resources of system 100 of FIG. 1. Of course requests not involving delegation of permissions of customer 201 can be processed as well.

Continuing with reference to FIG. 2a, the authorized delegate(s) 204 can be selected from a plurality of potential delegates 203. Potential delegates 203 can be chosen from a group or source such as a pool of delegates, that can include e.g., system host and/or 3rd party IT support staff, support staff identifiable (e.g., via stored attributes associated with each of one or more staff users in a set of such users and/or some grouping thereof) as having previously handled creation/correction issues relating the application/data of customer 201, such staff as might be identifiable according to a particular area of expertise, issue handling expertise and so on, as might relate to an issue or purpose currently affecting customer 201, for example.

Authorized delegate(s) 204 can be chosen based on applying one or more authorization filters 208 to the potential delegates 203 to arrive at one or more authorized delegate(s) 204. Applying the one or more filters 208 can include determining a correspondence between one or more attributes of a potential delegate 203 to one or more criterion in the one or more authorization filters 208. Delegate screening by filtering can be achieved by comparing (e.g., sufficiently in accordance with) potential delegates' attributes with criterion to determine suitability for access authorization. Such comparisons can be complete or by sufficiency (e.g., above or below some level, within some range, within N of a chosen criterion, etc.). One or more of the authorized delegate(s) 204 can be assigned to the request. The authorized delegate(s) assigned to the request can receive authorization to access computing resources of hosting system 100 allocated to the customer 201. An embodiment can add zero or more potential delegates 203 to a set of authorized delegate(s) 204 based upon attributes corresponding to criterion for example, thereby granting access to delegates where such access was not otherwise provided to such users and/or groups of users. In another embodiment, zero or more potential delegates 203 can be filtered out from further consideration for a particular request, ultimately arriving at a set of authorized delegate(s) 204, thereby limiting access to a broader collection of users and/or groups of users, and/or some combination thereof.

Criterion may be compared with attributes associated with individual users, subsets of users and/or the entire set of potential delegates enabling selection or screening of delegates by groups, sub-groups and/or combinations thereof. Attributes can be geopolitical attributes, such as citizenship, residency, employment status, employer, business, and/or other elements relating to personal history; geospatial attributes, such as present location, sales or service region location, worksite location, or other types of location based data; competency attributes, such as programming language proficiency, years of service or experience level, degrees or technical or professional certifications possessed and/or other qualification based attributes. Location based data may be expressed in latitude and longitude, distance from landmarks or other prominent locations, regions specified by boundaries delineated by points, altitudes and the like. In one embodiment, filtering can be performed based upon customer chosen criterion, non-customer chosen criterion, such as a criterion specified by a governmental or regulatory body for example, and/or various combinations of both customer chosen criteria and non-customer chosen criteria. By providing capabilities to "mix and match" disparate types of criteria, embodiments can enable issuing a closely tailored set of permissions to a select group of delegates. Thus, in embodiments, security of the systems can be enhanced.

Issuing an authorization 207 to an authorized delegate(s) 204 can include providing the delegate a link 209 with which to access computing resources allocated to the customer 201, such as data stored in the multi-tenant database 230, for example. Clicking link 209 enables the authorized delegate(s) 204 to gain access. Customer 201, in this example, can retain the ability to access the database 230. In some embodiments, issuing an authorization can also include enabling the delegate to impersonate the customer by combining a subset of permissions of the customer with those of the delegate. Activities of the delegate can be tracked to provide monitoring of the work that a delegate performs, creating an audit trail, and/or the like. In an embodiment, a delegate's activity can be compared against a request to determine whether the delegate successfully performed the steps of the request. In an embodiment, a delegate's activity can be compared against a request to determine whether the delegate performed any activities that were not part of the request. Such audit capabilities can enable embodiments to provide a quality indication for the delegate relative to achieving the request.

Figure 2B:
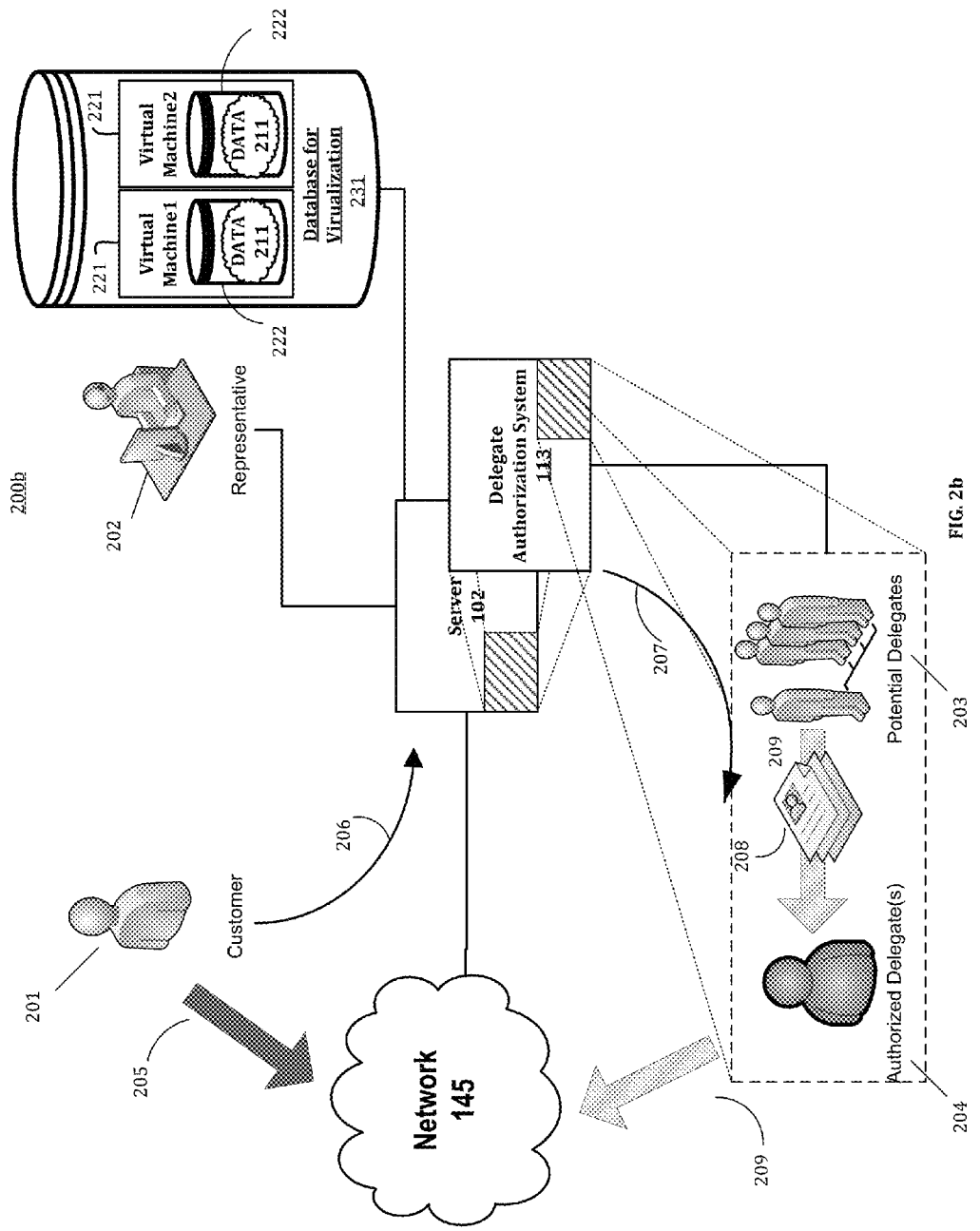
FIG. 2b is a flow diagram illustrating a hosting system embodiment in which the customer requests services and the authorized parties are notified and gain access.

Now turning to FIG. 2b, a block diagram of another example system embodiment 200b in which the customer requests services and authorized parties are notified and gain access is shown. Note that each of user 201, representative 202, potential delegates 203 and authorized delegate(s) 204, when communicating with system 200b, can communicate using a suitable client device, e.g., such as with client devices 140 of FIG. 1b, which are not shown in FIG. 2 for clarity sake. It will be appreciated that the directional arrows are not limiting and other, e.g., bi-directional, communication can also be conducted. For example a customer 201, who can be experiencing an issue, contacts representative 202 seeking assistance. The issue might involve a service issue, an audit request, a request for contract labor to be performed or the like. The representative 202 can be human, machine based proxy for human intervention or suitable combination thereof. Contact between customer 201 and representative 202 can be via telephone, email, an application and/or facilitated over a network or the like. In one application, the representative 202 is a support representative, for example, being contacted about a technical issue involving customer 201 attempting to access 205 (or otherwise work with) one or more cloud based computing resources of hosting system 100 of FIG. 1. Among other examples, the representative 202 can be a service representative, audit representative, contract labor representative or the like, being contacted by customer 201 to resolve some issue which requires access to computing resources of system 100 of FIG. 1. Customer 201 may, for example, be experiencing an issue while accessing one or more computing resources such as a database for virtualization 231, data 211, virtual database 222, customer virtual machine 221 or other computing resources in hosting system 100 via server 102 and network 145.

Continuing with reference to FIG. 2b, the authorized delegate(s) 204 can be selected from a plurality of potential delegates 203. Potential delegates 203 can be chosen from a group or source such as a pool of delegates, that can include e.g., system host and/or 3rd party IT support staff, support staff identifiable (e.g., via stored attributes associated with each of one or more staff users in a set of such users and/or some grouping thereof) as having previously handled creation/correction issues relating the application/data of customer 201, such staff as might be identifiable according to a particular area of expertise, issue handling expertise and so on, as might relate to an issue or purpose currently affecting customer 201, for example.

Authorized delegate(s) 204 can be chosen based on applying one or more authorization filters 208 to the potential delegates 203 to arrive at one or more authorized delegate(s) 204. Applying the one or more filters 208 can include determining a correspondence between one or more attributes of a potential delegate 203 to one or more criterion in the one or more authorization filters 208. Delegate screening by filtering can be achieved by comparing (e.g., sufficiently in accordance with) potential delegates' attributes with criterion to determine suitability for access authorization. Such comparisons can be complete or by sufficiency (e.g., above or below some level, within some range, within N of a chosen criterion, etc.). One or more of the authorized delegate(s) 204 can be assigned to the request. The authorized delegate(s) assigned to the request can receive authorization to access computing resources of hosting system 100 allocated to the customer 201. An embodiment can add zero or more potential delegates 203 to a set of authorized delegate(s) 204 based upon attributes corresponding to criterion for example, thereby granting access to delegates where such access was not otherwise provided to such users and/or groups of users. In another embodiment, zero or more potential delegates 203 can be filtered out from further consideration for a particular request, ultimately arriving at a set of authorized delegate(s) 204, thereby limiting access to a broader collection of users and/or groups of users, and/or some combination thereof.

Issuing an authorization 207 to the delegate(s) 204 can include providing the delegate 204, via a hyperlink 209, the ability to access customer data 211, which can be stored at least in part in a virtualized image database 221. In one embodiment, clicking link 209 accepts a grant to the delegate 204 access to the customer data 211. Issuing an authorization can also include enabling the delegate to impersonate the customer through combining permissions of the customer and the delegate. In some embodiments, activities of the delegate are tracked. This can be useful in monitoring the work that a delegate performs, creating an audit trail or the like.

Figure 2C:
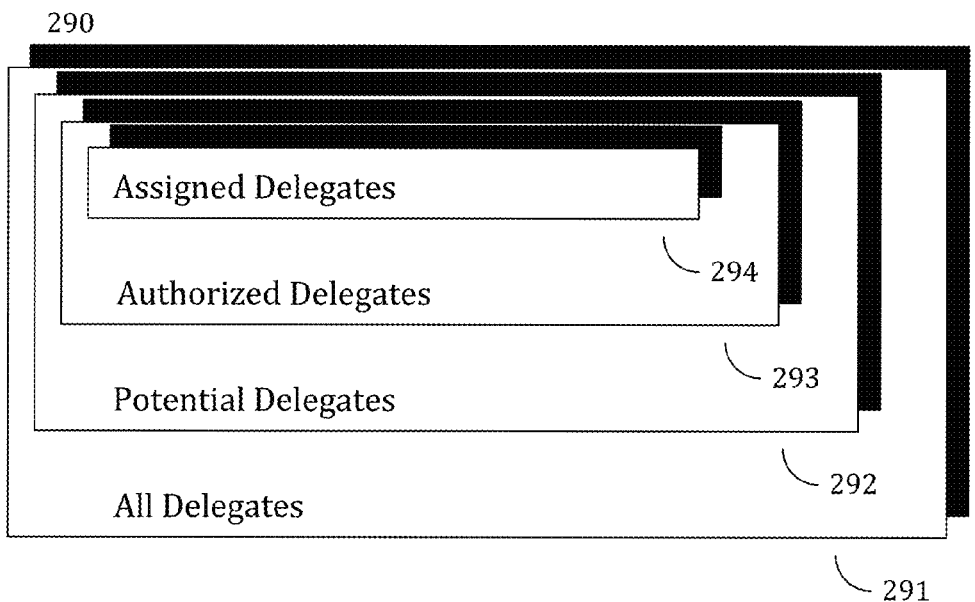
FIG. 2c is a block diagram of an example authorization system for delegates that can fall within other user groups that can have access to certain data.

FIG. 2c illustrates a block diagram of authorization system for delegates that can fall within other user groups that can have access to certain data. As show in FIG. 2c, a pool of potential delegates 292 can be determined within a larger delegate defined group 291. Possible bases for determining potential delegates include availability, workload, work shift, other, and/or combinations thereof. After at least one filter is applied to the group of potential delegates 292, a group of delegates meeting screening criterion of the filter, can be selected as authorized delegates 293. One or more authorized delegates are then assigned to access private customer data and designated as assigned delegates 294. These assigned delegates 294 can address the customer's request. Embodiments can implement a variety of applications since individual instances of customer-representative contact can occur for any of a variety of reasons, i.e., technical support, administrative changes, maintenance, general inquiries or the like.

Figure 3A:
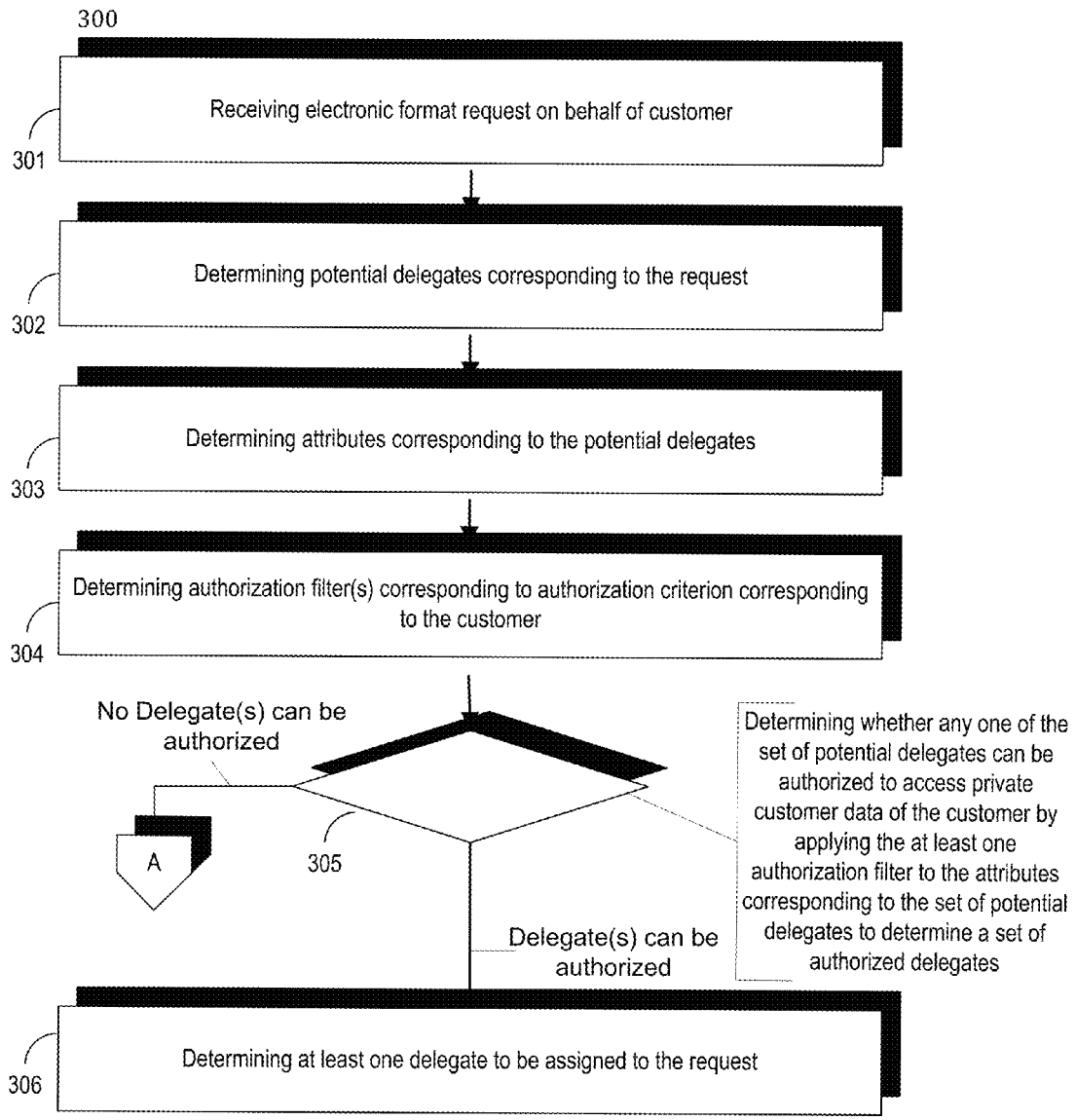
FIG. 3a is a flow diagram illustrating an example permission process in an embodiment.

FIG. 3a is a flow diagram illustrating an example permission process in an embodiment. As shown in FIG. 3a, a process 300, operatively disposed in delegate authorization system 113 and carried out upon one or more computing devices in system 100, grants to a delegate access to a customer database. In a block 301, an electronic format request made on behalf of a customer may be received. An electronic format request or a request expressed (or converted to) an electronic request can include any type of electronic communication in which some requests of given type can be ascertained from the communication. Requests can be entered into an electronic device or determined automatically from an electronic communication by analysis that flags something in the electronic communication. Common electronic formats can include a form with issue entry selection, which can be a field to be filled in, a drop down menu and/or other type of indication, an email or text message, a transcription of a telephone call, and other types of electronic formats.

In a block 302, one or more potential delegates corresponding to the request may be determined. Delegates can be charged with resolving a request, e.g., one or more of all requests, requests of certain type(s), requests of all customers, or requests of all members of a group(s) or subgroup(s) of customers having similar types of requests or other common characteristics. Potential delegates may be chosen for example from a pool of all agents of a host (cloud provider), a set of employee and/or third party agents that can be charged with acting on behalf of the customer or alternatively on behalf of the host.

In a block 303, attributes corresponding to the potential delegates may be determined. Attributes can be group attributes, e.g., customer service representatives, US citizens, and so forth; individual attributes, e.g., lives at 123 Mockingbird Lane; or combinations of both these types of attributes; or even simple attributes such as an employee name. Attributes can be geopolitical attributes, such as citizenship, residency, employment status, employer, business, and/or other elements relating to personal history; geospatial attributes, such as present location, sales or service region location, worksite location, or other types of location based data; competency attributes, such as programming language proficiency, years of service or experience level, degrees or technical or professional certifications possessed and/or other qualification based attributes. Location based data may be expressed in latitude and longitude, distance from landmarks or other prominent locations, regions specified by boundaries delineated by points, altitudes and the like. Attributes can be associated with individual users, subsets of users and/or the entire set of potential delegates to provide the capability of determining potential delegates based upon groups or subgroups.

In a block 304, authorization filter(s) corresponding to authorization criterion corresponding to the customer may be determined. An authorization filter can include one or more authorization criterion corresponding to the customer. For example, an authorization filter can include a criterion to express: "Customer XYZ requires citizens of the USA". Criterion for selection based on attribute(s) can be chosen by a customer, and/or a non-customer, such as a host provider, governmental or other regulatory body, labor organization or the like, or various combinations thereof.

In a block 305, it can be determined whether any one of the set of potential delegates can be authorized to access private customer data of the customer by applying the at least one authorization filter to the attributes corresponding to the set of potential delegates to determine a set of authorized delegates. Authorized delegates can be selected based at least upon a correspondence between one or more of the attributes of the potential delegate(s) to one or more criterion. Various embodiments can add zero or more potential delegates to a set of authorized delegate(s), thereby granting access to delegates where such access was not otherwise provided to such users and/or groups of users, filter out zero or more potential delegates from further consideration thereby limiting access to a broader collection of users and/or groups of users, and/or some combination thereof.

In a block 306, at least one delegate to be assigned to the request may be determined. Various embodiments also provide for limiting or providing greater access capability to all or some of the user data by one or more of the delegates according to one or more stages of such analysis and, in the event that a suitable delegate cannot be found, for the system to implement appropriate action in the form of an exception handling strategy that can be invoked in an automatic manner and/or with user intervention. For example, in the event that a suitable cannot be found, the request can be denied. Alternatively, a status message can be posted indicating which criterion cannot be satisfied in the event that a suitable delegate cannot be determined. In another course of action, a prompt can be provided for an approval to grant limited access privileges to a delegate in the event that no delegate meets all criteria. Once a delegate has accomplished tasks comprising the request, the delegate's authorization can be removed, extended and/or renewed by delegate authorization and tracking engine 411 described further with reference to FIG. 4b below. In an embodiment, delegates can be authorized to authorize other potential delegates that otherwise meet the criteria.

Once a delegated user has been assigned, a link that enables the delegate to access the private customer data and impersonate the customer can be generated. The link can be made available to the one or more delegates assigned to the request. When accessed, the link can allow a delegate to access computing resources allocated to the customer, such as private customer data, for example. An embodiment authorization includes enabling the delegate to impersonate the customer. The activities of the delegate can be tracked and activities of multiple delegates can be tracked to each delegate. The tracking of activities can include generating an audit trail for example. Tracking the delegate's actions can enable embodiments to provide accountably, support feedback, or enable changes to be reverted.

Figure 4A:
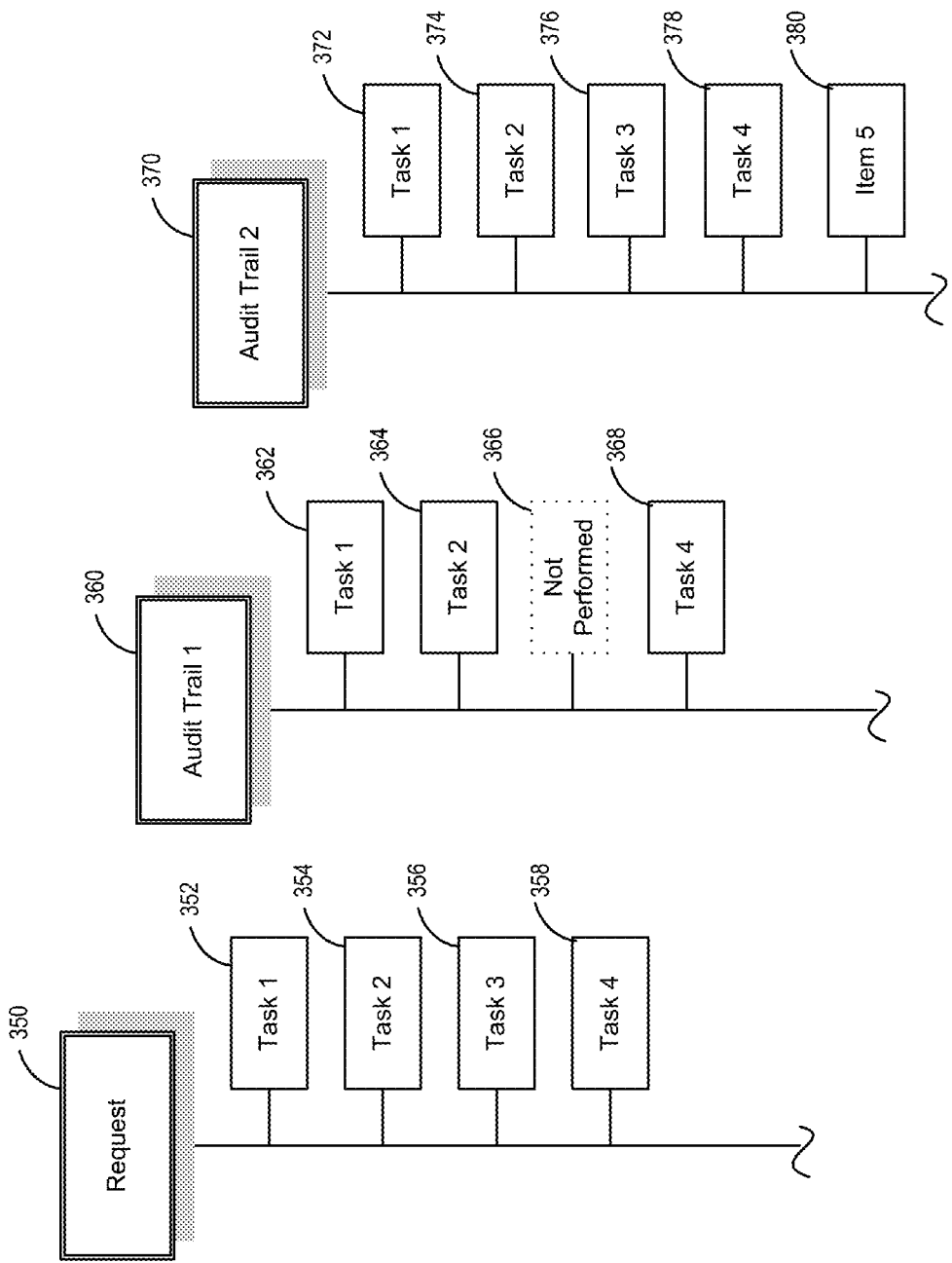
FIG. 4a illustrates a block diagram of various tasks and/or functionality comprising a request and various exemplary audit trails provided by an embodiment.

Tracking can enable a delegate's activity to be compared against a request in order to determine whether the delegate successfully performed the steps of the request, and/or whether the delegate performed any activities that were not part of the request. FIG. 4a illustrates a block diagram of various tasks and/or functionality comprising a request and various exemplary audit trails provided by an embodiment. As shown in FIG. 4a, a request 350 includes a variety of tasks (352, 354, 356, 358). Tasks capable of being associated with a request can be specified using a taxonomy or the like for example. Relationships between tasks and corresponding requests can be tracked using any of a variety of constructs familiar to the computing arts such as databases, relational or other, linked data structures such as linked lists, trees, etc., graphs, and/or combinations thereof. Requests and tasks definitions can be created by customers, representatives, and/or combinations thereof using any of a variety of techniques such as editors, input screens and prompts, parsers and tokenizers analyzing natural language text and/or combinations thereof.

Now further with reference to FIG. 4a, once exemplary request 350 has been submitted and a delegate has acted, the resulting audit trail 1 (360) can be compared with request 350 to verify correspondence between tasks (352, 354, 358) with completed tasks (362, 364, 368). This example illustrates that correspondence checking will reveal that task 356 which comprises request 350 is missing from audit trail 1 (360) and illustrated by "Not Performed" box 366. Turning now to audit trail 2 (370), an example situation is shown in which correspondence checking will reveal the presence of an extra item 380 in audit trail 2 (370). Item 380 is not specified in request 350, so it indicates that a delegate may have undertaken an undesirable operation—inadvertently or otherwise—that was not specified as part of the original request. Such audit capabilities can enable embodiments to provide a quality indication for the delegate relative to achieving the request.

Figure 3B:
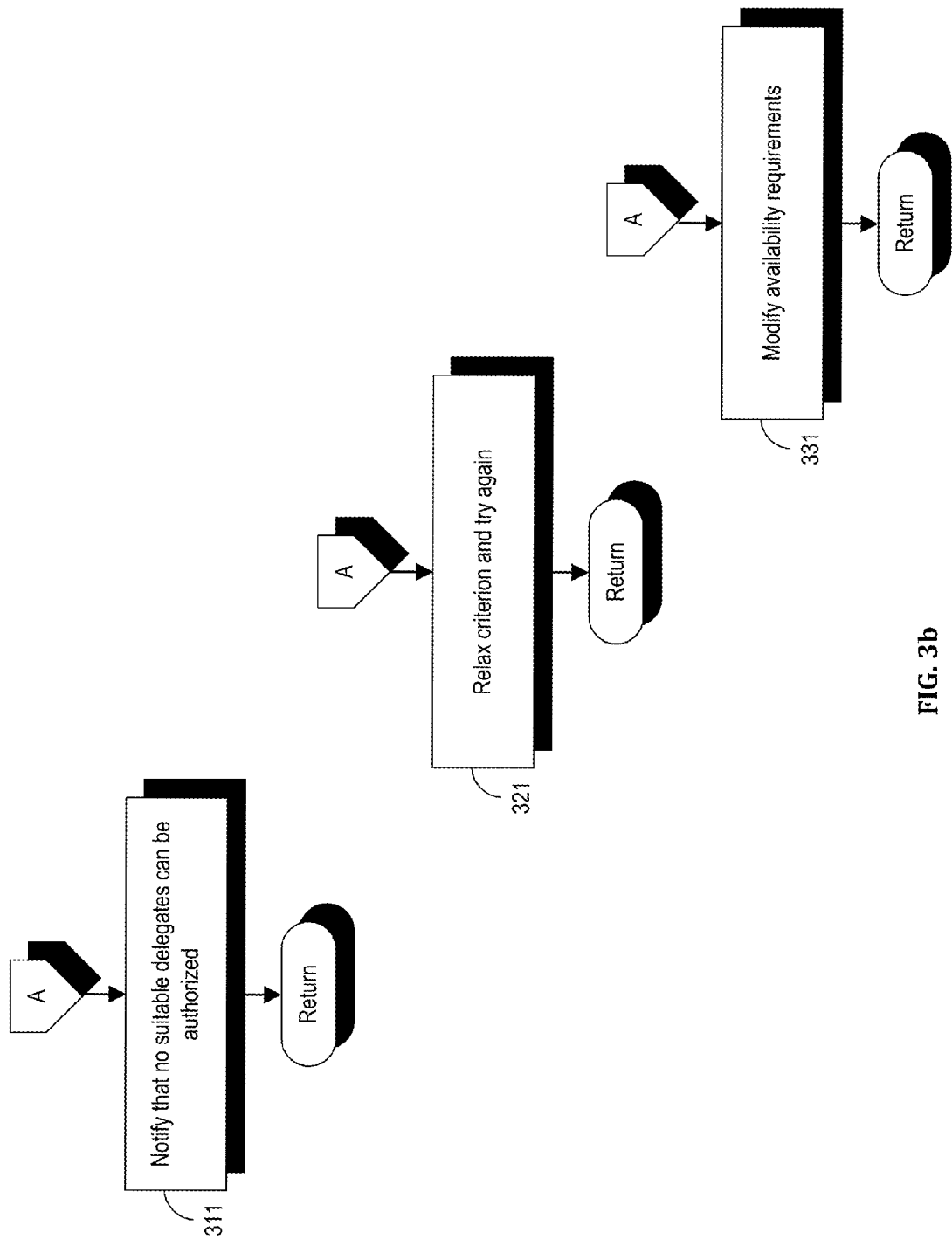
FIG. 3b is a flow diagram illustrating flow charts for example exception handling strategies in embodiments.

While in an embodiment ensuring that at least some delegates will be available can be provided for in accordance with an agreement between the cloud provider—or a third party—and the customer, other embodiments can include exception handling strategies for handling the condition that no available delegates meet the criterion. FIG. 3b is a block diagram illustrating flow charts for example exception handling strategies when no delegate meets the criterion for authorization in block 305 of FIG. 3a. In block 311, a notification that no delegates can be authorized is provided. Notifying can be used alone or in addition to taking another course of action, such as illustrated in block 321, in which one or more criterion are relaxed, in some order or according to a priority, and screening is attempted again. In block 331, another exception handling strategy is shown in which the number of delegates from which to choose can be increased by modifying availability requirements, e.g., accepting off shift persons, or persons in inconvenient time zones, etc. as potential delegates and/or shifting a time to service the request so that a suitable delegate is available in the event that no delegate meets all criteria. An embodiment includes tracking an exception handling process so that exceptions can be auditable. Exception handling strategies vary widely, and can be used alone or in conjunction with one another, in various embodiments, thus the strategies shown in FIG. 3b are intended merely as examples of possible strategies that can be employed.

Figure 4B:
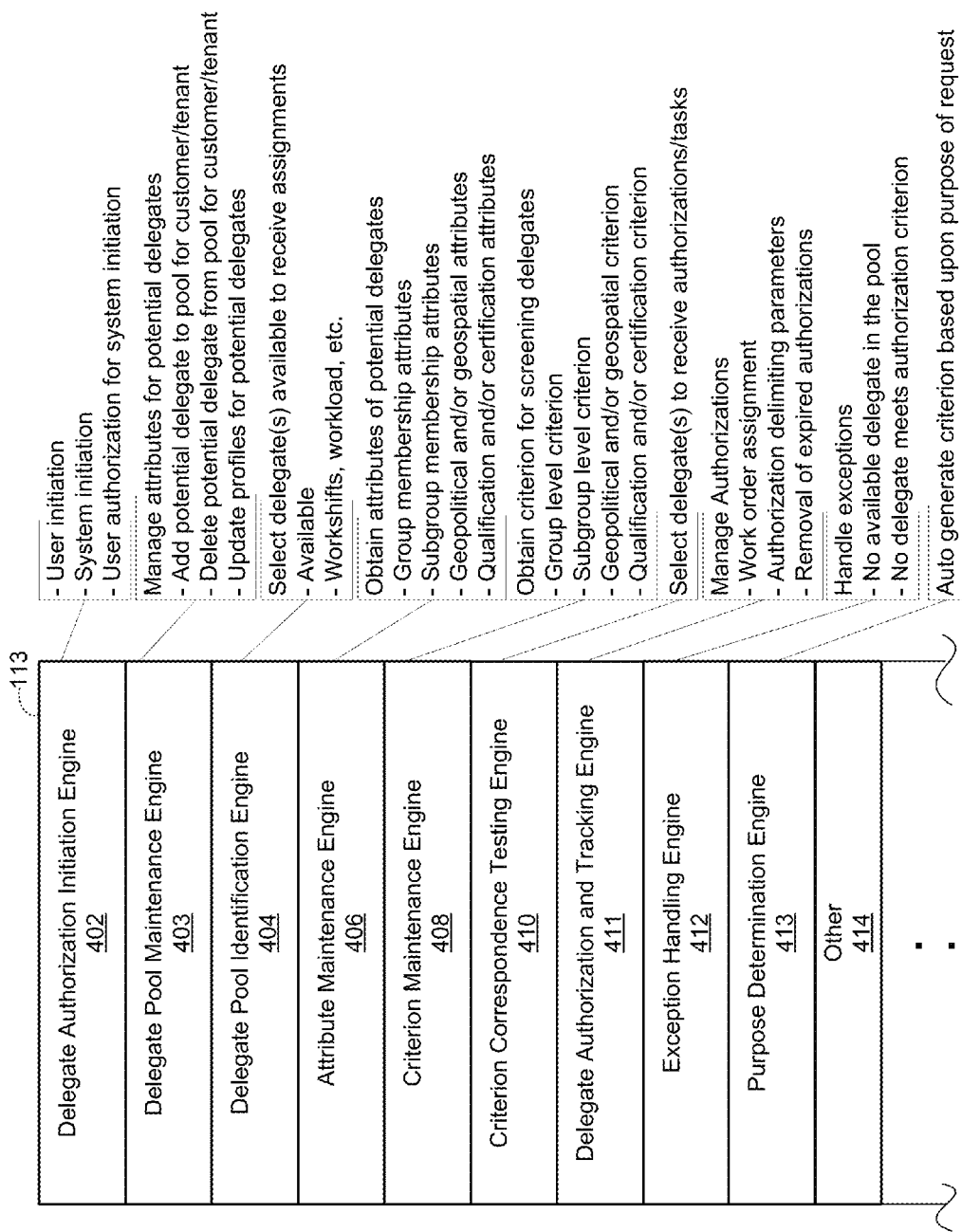
FIG. 4b illustrates a block diagram of various engines implementing features and/or functionality provided by a delegate authorization system embodiment.

FIG. 4b illustrates a block diagram of various engines implementing features and/or functionality provided by a delegate authorization system embodiment. As show by FIG. 4b, delegate authorization system 113 includes a delegate authorization initiation engine 402 that provides initiation and housekeeping functionality such as user initiation, system initiation and user authorization for system initiation, and the like.

Delegate pool maintenance engine 403 provides for managing attributes for potential delegates, for example adding potential delegate(s) to the pool for customer/tenant, deleting potential delegate(s) from the pool for customer/tenant, updating profiles for potential delegate(s) in the pool, automatically updating delegate attributes based upon experience gained, time and/or tasks scheduled, coursework completed, certifications attained, prior work with a customer/tenant, and the like.

Delegate pool identification engine 404 provides for selecting delegate(s) available to receive assignments. Delegates may be selected based upon availability, work shift, workload and the like.

Attribute maintenance engine 406 provides for obtaining attributes of potential delegates, for example, group membership attributes, e.g., customer/host/trusted third party agents/affiliates, etc., sub-group membership attributes, geopolitical attributes, geospatial attributes, qualification attributes, certification attributes, other attributes and/or combinations thereof.

Criterion maintenance engine 408 provides for obtaining criterion for screening delegates including criterion for adding screened delegates in and/or criterion for filtering delegates out, such as group level criterion, sub-group level criterion, geopolitical criterion, geospatial criterion, qualification criterion, certification criterion, other criterion and combinations thereof.

Criterion correspondence testing engine 410 provides for selection of delegate(s) to receive authorization including adding screened delegates in or filtering delegates out based upon screening.

Delegate authorization and tracking engine 411 provides for managing authorizations including work order assignment, authorization delimiting parameters defining authorizations to be made, removal of expired authorizations based upon one or more of access, time, task, content security level, delegate security level, exclusions, sandbox, and/or combinations thereof, extensions, renewals, subscriptions and/or other authorization management tasks and/or combinations thereof.

Exception handling engine 412 provides for handling of exception conditions arising during selection and authorizing delegates. For example, an exception may occur when there are no available delegates in the potential delegate pool. This situation can arise during a work stoppage, holiday, inclement weather or so forth. Another exception condition can occur when no delegate meets the authorization criteria. Possible exception handling strategies for this type of exception include notification only or in addition to taking another course of action such as relaxing one or more criterion in some order or according to a priority, or increasing the number of delegates to choose from by modifying availability requirements, e.g., accepting off shift persons as delegates, etc and/or shifting a time to service the request so that a suitable delegate is available in the event that no delegate meets all criteria for example. An embodiment tracks the exception handling process so that exceptions can be auditable.

A Purpose Engine 413 provides identification of purpose of a request in order to further automate selection of delegates. Purpose engine 413 can include one or more models for analyzing communication to determine a purpose of the request and assign appropriate delegates. Models such as speech recognition techniques, natural language processing, fuzzy logic, term recognition or search and/or combinations of these and other communications or other semantic analysis techniques, many of which are useful for analyzing communications to identify meaning. Other engines(s) 414 may also comprise delegate authorization system 113.

Figure 5A:
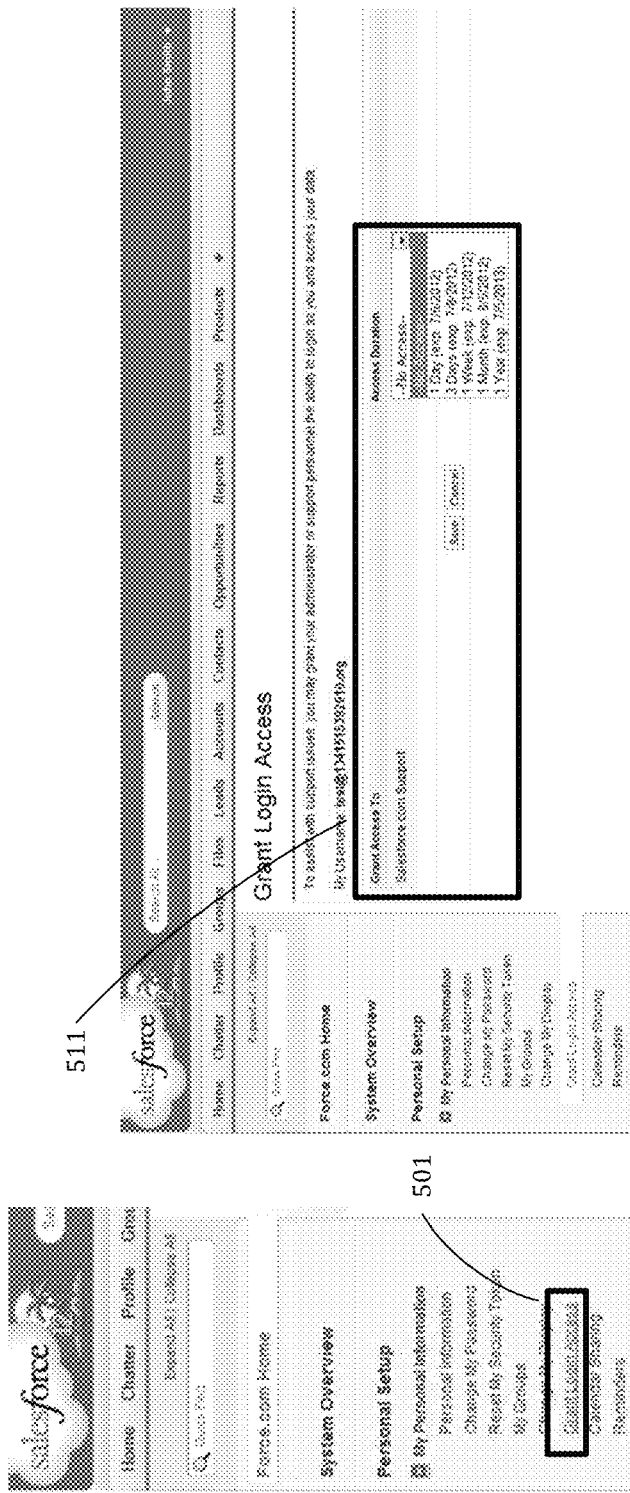
FIGS. 5a-5d are screen shots depicting example screens employed in a process of granting access to a delegate and tracking an audit trail of delegate actions in embodiments.

FIGS. 5a-5d are screen shots depicting example screens employed in a process of granting access to a delegate and tracking an audit trail of delegate actions in an embodiment. FIG. 5a shows an example screen used by a process embodiment for granting access to private customer data. By clicking link 501 on screen shown in FIG. 5a, an administrator or other authorized person at the customer causes a box 511 to be displayed. Working with the items in the box 511, access to customer computing resources can be delegated. For example, the customer might provide access to the delegate for a period of 1 day, 3 days, 1 month, or 1 year using the selection mechanisms encompassed by box 511. This grant of access can be revoked later if desired of course. Once the customer grants access using box 511a delegate can be assigned appropriate authorization levels to customer private data.

Figure 5B:
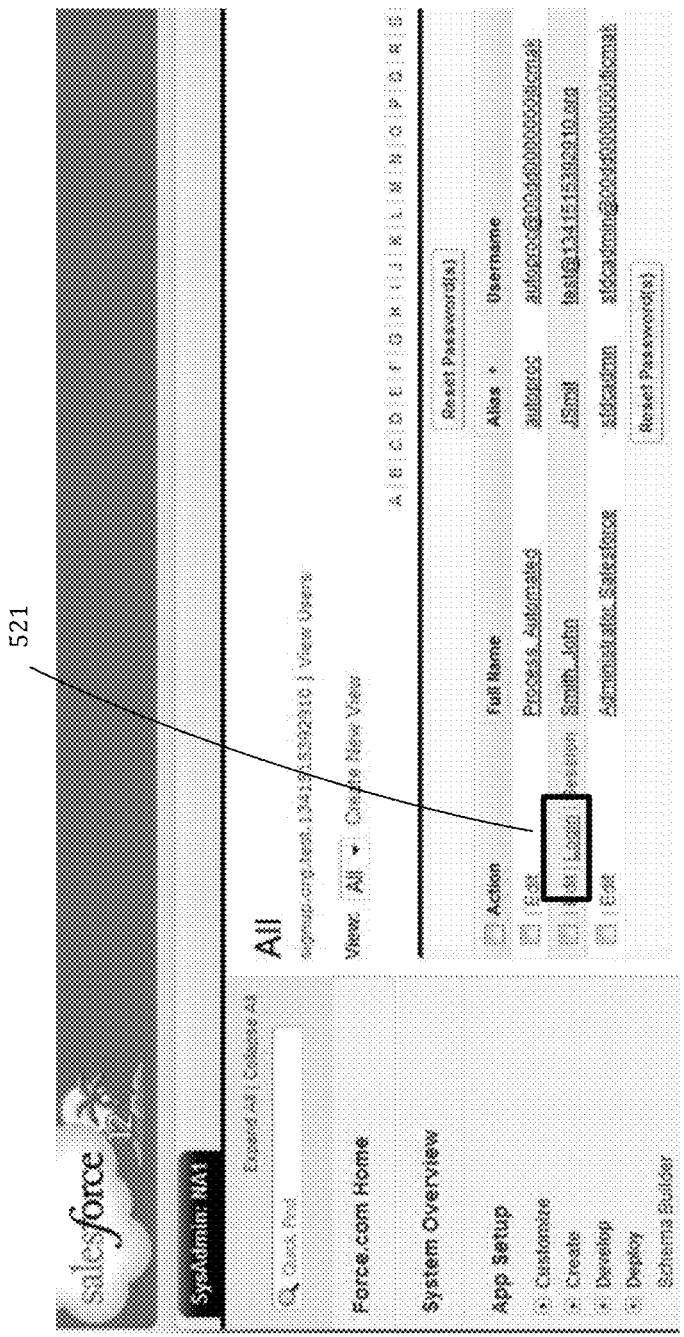
Figure 5C:
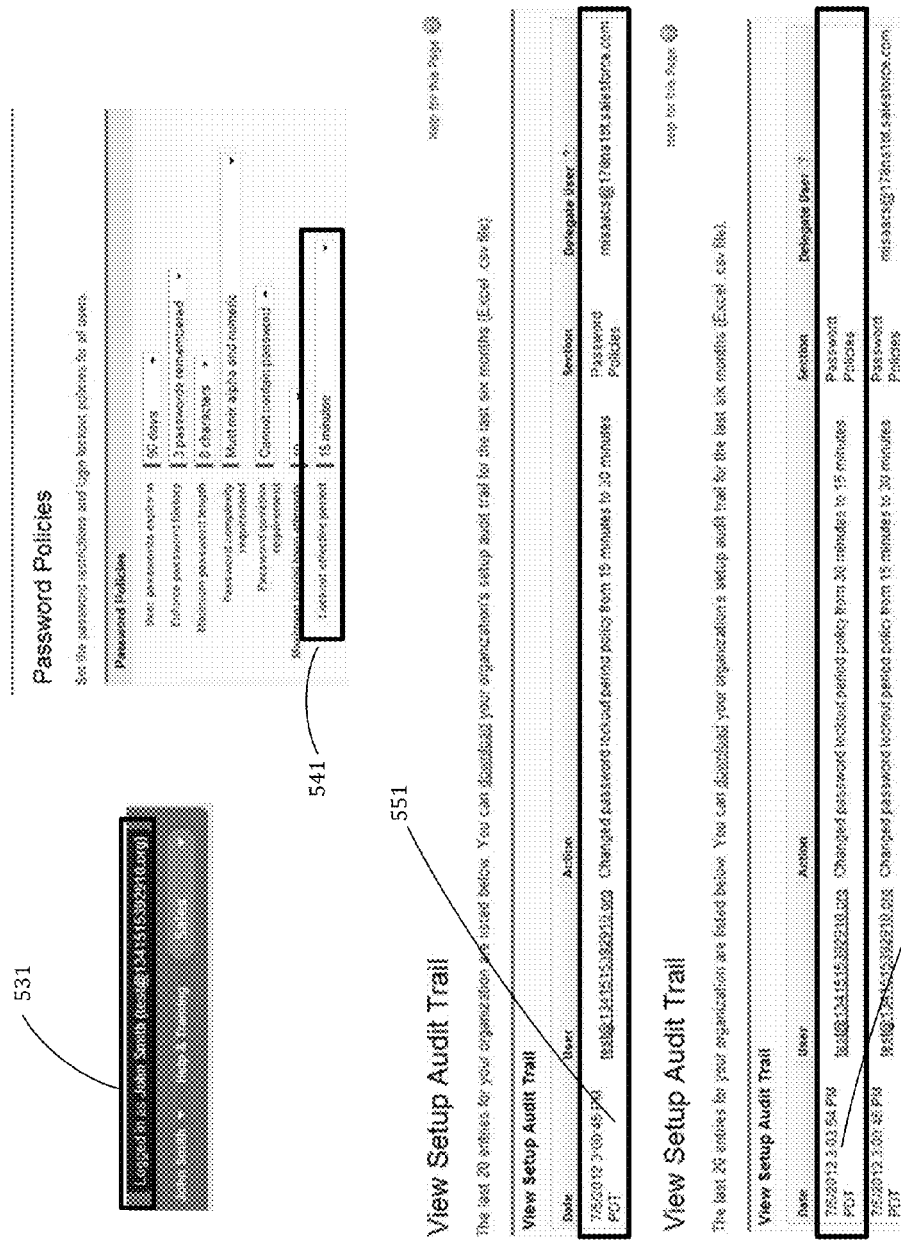

In FIG. 5b, an example screen used a process embodiment for providing an assigned delegate a capability to receive access to private customer data. As show in FIG. 5b, an embodiment provides a login link 521 that appears to an assigned delegate. The delegate can click the login link 521 to obtain the capability to access customer computing resources such as private customer data. Some implementations will enable the assigned delegate to impersonate the customer. As shown in FIG. 5c, an embodiment providing user impersonation capability can include a display mechanism 531 indicating the person being impersonated. Embodiments can provide for audit of a delegate's activities even in instances when the delegate is impersonating a user. In an embodiment, a delegate's activity log can be compared against a request to determine whether the delegate successfully performed the steps of the request. In an embodiment, a delegate's activity log can be compared against a request to determine whether the delegate performed any activities that were not part of the request. Such audit capabilities can enable embodiments to provide a quality measure for the delegate relative to achieving the request.

Further with reference to FIG. 5c, the assigned delegate impersonating a customer that be monitored to form an audit trail to track the delegate's activities in an embodiment. If, for example, an assigned delegate changes password policies to adjust the lockout effective period 541 from 15 minutes to 30 minutes, a setup audit trail 551 can provide display of tracking for that change as originating from the delegate impersonating the customer account. As shown in 551, the customer user "test" is shown as having taken the action of changing the password lockout period policy from 15 minutes to 30 minutes. The action is correctly tracked however to delegate "misaacs" impersonating the customer account. If, for example, the customer changed the password lockout period policy back from 30 minutes to 15 minutes, the action is correctly tracked to only the customer and not the delegate 561.

Figure 5D:
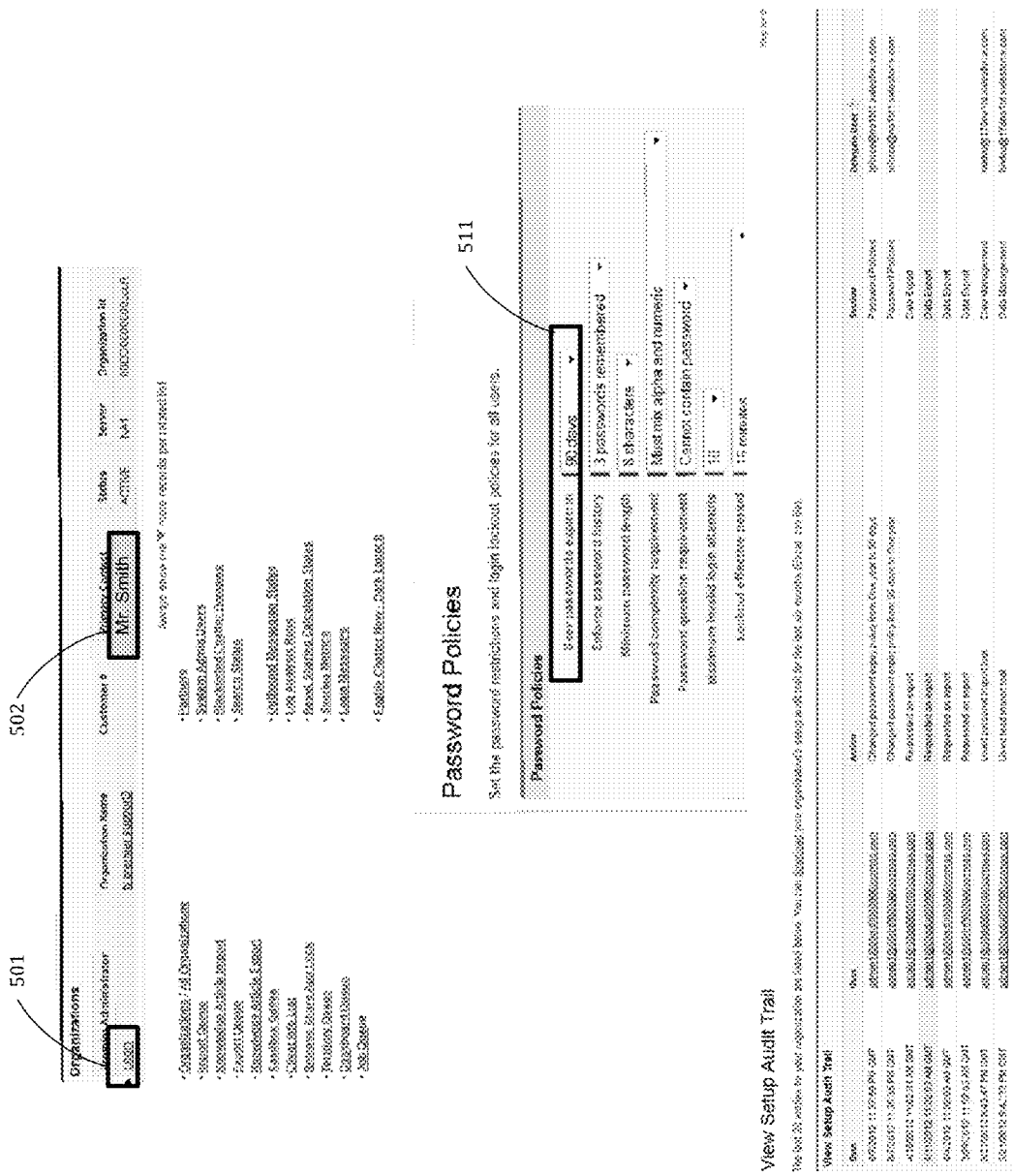

FIG. 5d illustrates a premier support delegate login screen embodiment. A login link 501 is only visible to authorized delegates 204. For non-authorized users, login link 501 does not appear on the delegate's SysAdmin page. In this embodiment, the login link facilitates easy access to customer data, such as stored in database 230 or 231 for example, without the customer having to grant ad hoc access permission. Security of the customer data is not compromised because the login link is only visible to authorized delegates 204 with customer approved or authorized permissions.

Once the authorized delegate 204 has logged in with the login link 501, the delegate can change, for example, the user password expiry policy from 90 days to one year 511. A setup audit trail will track this change in policy 521. The audit trail also denotes which delegate made the change, in this case "ipforce" instead of the primary contact 502 "Mr. Smith" as seen making other changes 522. However, both delegates were recorded as user "admin1" in the audit trail but their true identity is also noted.

In another exemplary embodiment, the customer 201 has limited control over a support delegate account that allows delegate(s) 204 to access the customer database 230 or 231. In this example, the customer 201 only has control over what data the delegate 204 can access and the customer 201 does not have access over the administration of the delegate 204 account. The customer support account is maintained by the hosting system provider while the support account exists in the database organization. The support account is only available to customers who subscribe to the premier service. If a customer does not subscribe, the hosting system has the ability to terminate the support service. While a customer 201 has ultimate control over the access to customer specific data, the customer 201 cannot control the support account assigned by the infrastructure provider to the customer account. This division of permissions allows for easy access to the customer database by support delegates while preventing the customer 201 from abusing the assigned support account.

Figure 6:
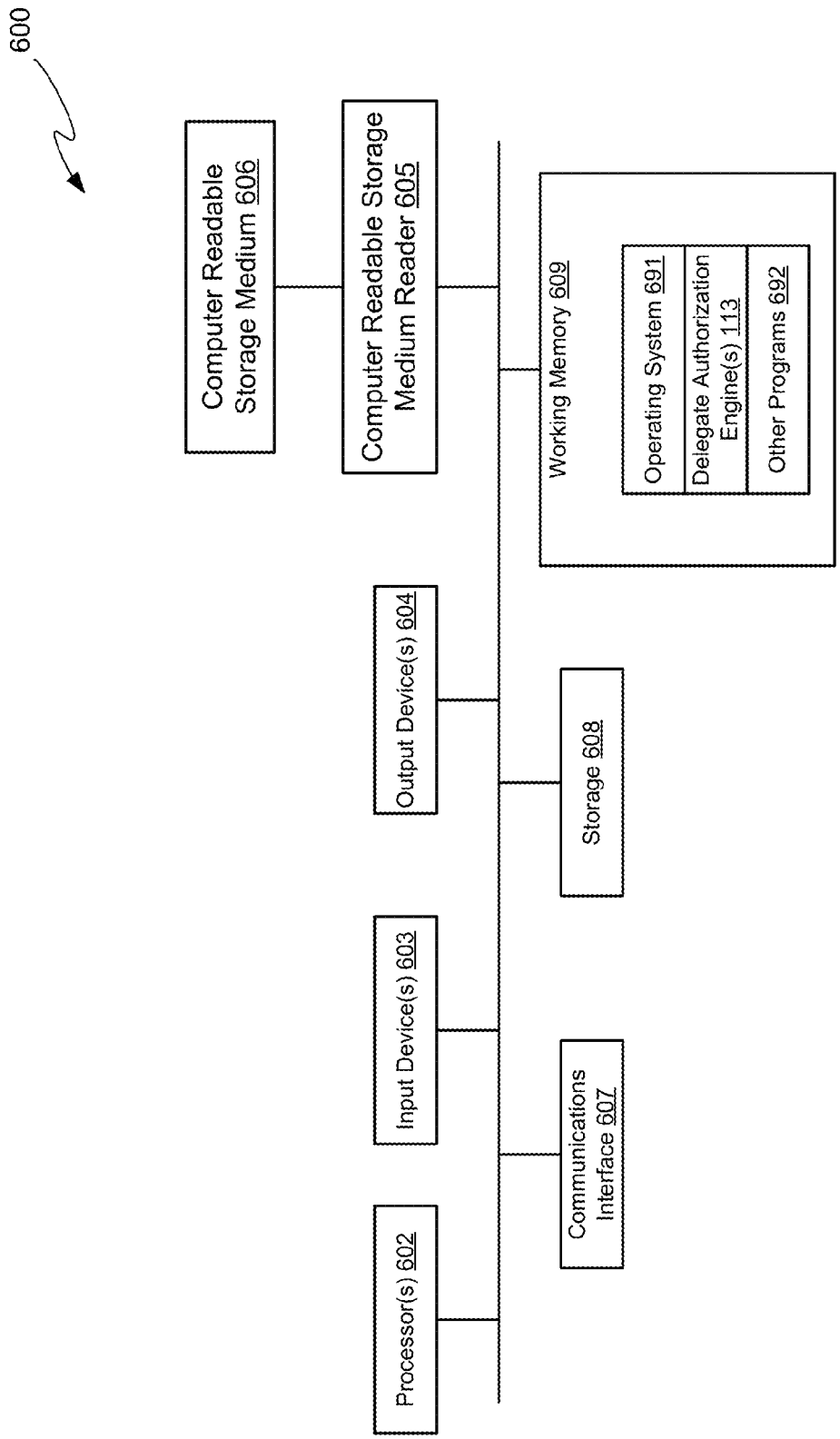
FIG. 6 illustrates an exemplary computing system that can comprise one or more of the elements shown in FIG. 1.

FIG. 6 illustrates an exemplary computing system 600, such as a PC (or other suitable "processing" system), that can comprise one or more of the elements shown in FIG. 1. While other application-specific device/process alternatives might be utilized, such as those already noted, it will be presumed for clarity sake that system 100 elements (FIG. 1) are implemented by one or more processing systems consistent therewith, unless otherwise indicated.

As shown, computer system 600 comprises elements coupled via communication channels (e.g. bus 601) including one or more general or special purpose processors 602, such as a Pentium® or Power PC®, digital signal processor ("DSP"), or other processing. System 600 elements also include one or more input devices 603 (such as a mouse, keyboard, joystick, microphone, remote control unit, tactile, biometric or other sensors, and so on), and one or more output devices 604, such as a suitable display, joystick feedback components, speakers, biometric or other actuators, and so on, in accordance with a particular application.

System 600 elements also include a computer readable storage media reader 205 coupled to a computer readable storage medium 606, such as a storage/memory device or hard or removable storage/memory media; examples are further indicated separately as storage device 608 and memory 609, which can include hard disk variants, floppy/compact disk variants, digital versatile disk ("DVD") variants, smart cards, read only memory, random access memory, cache memory or others, in accordance with a particular application (e.g. see data store 130 of FIG. 1). One or more suitable communication devices 607 can also be included, such as a modem, DSL, infrared, etc. for providing inter-device communication directly or via suitable private or public networks, such as the Internet. Working memory 609 is further indicated as including an operating system ("OS") 691, delegate authorization engine(s) 113 and other programs 692, such as application programs, mobile code, data, or other information for implementing system 100 elements, which might be stored or loaded therein during use.

System 600 element implementations can include hardware, software, firmware or a suitable combination. When implemented in software (e.g. as an application program, object, downloadable, servlet, and so on, in whole or part), a system 600 element can be communicated transitionally or more persistently from local or remote storage to memory for execution, or another suitable mechanism can be utilized, and elements can be implemented in compiled, simulated, interpretive or other suitable forms. Input, intermediate or resulting data or functional elements can further reside more transitionally or more persistently in a storage media or memory, (e.g. storage device 608 or memory 609) in accordance with a particular application.

Certain potential delegate finding, delegate selection, authorization issuance and other aspects enabled by input/output processors and other element embodiments disclosed herein can also be provided in a manner that enables a high degree of broad or even global applicability; these can also be suitably implemented at a lower hardware/software layer. Note, however, that aspects of such elements can also be more closely linked to a particular application type or machine, or might benefit from the use of mobile code, among other considerations; a more distributed or loosely coupled correspondence of such elements with OS processes might thus be more desirable in such cases.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method for granting access to private customer data, the method comprising:
   receiving, by a database system, an electronic format request on behalf of a customer, the electronic format request being a request to perform a task using a subset of private data of the customer, the private data being cloud data stored on the database system;
   identifying, by the database system, a plurality of potential delegates corresponding to the electronic format request, the plurality of potential delegates having no access to the private data unless authorization is provided to the plurality of potential delegates, the plurality of potential delegates being identified based on an ability to resolve the electronic format request;
   determining, by the database system, attributes corresponding to the plurality of potential delegates, the attributes relating to the identity of a corresponding potential delegate;
   determining, by the database system, at least one authorization filter, the at least one filter including customer-specific authorization criterion pertaining to desired attributes;
   applying the at least one authorization filter to the attributes corresponding to the plurality of potential delegates to determine a set of authorized delegates, based at least in part on determining a correspondence between at least one of the attributes to at least one of the authorization criterion;
   determining, by the database system, from the set of authorized delegates, at least one delegate to be assigned to resolve the electronic format request, and
   issuing an authorization to the at least one delegate to be assigned to the electronic format request, wherein issuing an authorization includes providing authorization for reviewing the subset of private data of the customer and providing a link facilitating login as the at least one delegate.

2. The method of claim 1, wherein providing authorization for reviewing at least a subset of private data of the customer includes:
   granting to the delegate a permission of the customer.

3. The method of claim 2, further comprising:
   tracking activities of the delegate.

4. The method of claim 1, wherein determining at least one authorization filter, the at least one filter including authorization criterion corresponding to the customer, includes:
   determining an authorization filter including at least one authorization criterion chosen by a customer.

5. The method of claim 1, wherein determining at least one authorization filter, the at least one filter including criterion corresponding to the customer, includes:
   determining an authorization filter including at least one authorization criterion chose by a non-customer.

6. The method of claim 1, wherein the applying the at least one authorization filter to the attributes corresponding to the plurality of potential delegates to determine a set of authorized delegates, based at least in part on determining a correspondence between at least one of the attributes to at least one of the criterion includes:
  determining whether a potential delegate can be added to the set of authorized delegates based at least in part upon the correspondence between at least one of the attributes to at least one of criterion.

7. The method of claim 1, wherein the applying the at least one authorization filter to the attributes corresponding to the plurality of potential delegates to determine a set of authorized delegates, based at least in part on determining a correspondence between at least one of the attributes to at least one of the criterion, includes:
  determining whether a potential delegate is to be deleted from the set of authorized delegates based at least in part upon the correspondence between at least one of the attributes to at least one of the criterion.

8. The method of claim 1, wherein issuing an authorization to the at least one delegate to be assigned to the electronic format request, includes:
  providing a link facilitating login as the delegate.

9. The method of claim 1, further comprising:
  determining, by the database system, a second delegate; and
  tracking, by the database system, activities of each delegate.

10. The method of claim 1, further comprising:
  receiving, by the database system, a second electronic format request;
  determining, by the database system, at least one element in the second electronic format request common to the first electronic request; and
  issuing, by the database system, a second authorization to the at least one delegate to be assigned to the second electronic format request, based at least in part on determining that the at least one element in the second electronic format request is common to the first electronic request.

11. The method of claim 1, wherein receiving an electronic format request includes:
  receiving at least one of a request expressed in electronic format, and a request converted into a request expressed in electronic format.

12. The method of claim 1, further comprising:
  terminating, by the database system, authorization when the customer is not subscribed to a support service.

13. The method of claim 1, wherein the applying the at least one authorization filter to the attributes corresponding to the plurality of potential delegates to determine a set of authorized delegates, based at least in part on determining a correspondence between at least one of the attributes to at least one of the criterion, includes:
  determining correspondence between an attribute and a geo-graphical or geo-political criterion.

14. The method of claim 1, wherein the applying the at least authorization filter to the attributes corresponding to the plurality of potential delegates to determine a set of authorized delegates, based at least in part on determining a correspondence between at least one of the attributes to at least one of the authorization criterion, includes:
  determining correspondence between an attribute and at least one of: citizenship, residency, employment status, employer, business, and criminal history.

15. The method of claim 1, further comprising:
  invoking, by the database system, an exception handling strategy for the request in the event that a suitable delegate cannot be determined.

16. The method of claim 15, further comprising:
  tracking, by the database system, an exception handling process thereby enabling exceptions to be auditable.

17. The method of claim 14, wherein invoking an exception handling strategy for the request includes:
  providing a status message indicating which criterion could not be satisfied in the event that a suitable delegate could not be determined.

18. The method of claim 14, wherein invoking an exception handling strategy for the request includes:
  shifting a time to service the request so that a suitable delegate is available in the event that no delegate meets all criteria.

19. A computer-implemented method for granting access to private customer data, the method comprising:
  receiving, by a database system, via a computing device an electronic format request on behalf of a customer, the electronic format request being a request to perform a task using a subset of private data of the customer, the private data being cloud data stored on the database system;
  identifying, by the database system, a plurality of potential delegates corresponding to the electronic format request, the plurality of potential delegates having no access to the private data unless authorization is provided to the plurality of potential delegates, the plurality of potential delegates being identified based on an ability to resolve the electronic format request;
  determining, by the database system, attributes corresponding to the plurality of potential delegates, the attributes relating to the identity of a corresponding potential delegate;
  determining, by the database system, at least one authorization filter, the at least one filter including customer-specific authorization criterion pertaining to desired attributes;
  applying the at least one authorization filter to the attributes corresponding to the plurality of potential delegates to determine a set of authorized delegates, based at least in part on determining a correspondence between at least one of the attributes to at least one of the authorization criterion;
  determining, by the database system, from the set of authorized delegates, at least one delegate to be assigned to resolve the electronic format request;
  issuing, by the database system, an authorization to the at least one delegate to be assigned to the electronic format request, wherein issuing an authorization includes providing authorization for reviewing the a subset of private data of the customer;
  granting, by the database system, the at least one delegate access to the private data of the customer by providing a link facilitating login as the at least one delegate; and
  providing, by the database system, the at least one delegate at least one permission of the customer to enable the at least one delegate to impersonate a user at the customer while tracking activities of the at least one delegate.

20. A non-transitory machine readable medium, storing one or more instructions which when executed by one or more processors cause the one or more processors to perform the following:
  receiving via a computing device an electronic format request on behalf of a customer, the electronic format request being a request to perform a task using a subset of private data of the customer, the private data being cloud data stored on the database system;

identifying, by the database system, a plurality of potential delegates corresponding to the electronic format request, the plurality of potential delegates having no access to the private data unless authorization is provided to the plurality of potential delegates, the plurality of potential delegates being identified based on an ability to resolve the electronic format request;

determining attributes corresponding to the plurality of potential delegates, the attributes relating to the identity of a corresponding potential delegate;

determining, by the database system, at least one authorization filter, the at least one filter including customer-specific authorization criterion pertaining to desired attributes;

applying the at least one authorization filter to the attributes corresponding to the plurality of potential delegates to determine a set of authorized delegates, based at least in part on determining a correspondence between at least one of the attributes to at least one of the authorization criterion;

determining, from the set of authorized delegates, at least one delegate to be assigned to resolve the electronic format request;

issuing an authorization to the at least one delegate to be assigned to the electronic format request, wherein issuing an authorization includes providing authorization for reviewing the subset of private data of the customer;

granting the at least one delegate access to the private data of the customer to enable the at least one delegate to impersonate a user at the customer while tracking activities of the at least one delegate.

21. A computer-implemented method for determining a number of candidates available to meet a criterion of interest, comprising:

receiving, by a database system, a criterion of interest on behalf of a customer, the criterion of interest pertaining to desired attributes;

identifying, by the database system, a plurality of potential delegates corresponding to the criterion of interest, the plurality of potential delegates having no access to private data of the customer unless authorization is provided to the potential delegate, the plurality of potential delegates being identified based on an ability to resolve a received electronic format request to perform a task using a subset of the private data of the customer, the private data being cloud data stored on the database system;

determining, by the database system, attributes corresponding to the plurality of potential delegates, the attributes relating to the identity of a corresponding potential delegate;

determining, by the database system, at least one authorization filter, the at least one filter including authorization criterion that comprises the criterion of interest;

applying the at least one authorization filter to the attributes corresponding to the plurality of potential delegates to determine a set of authorized delegates, based at least in part on determining a correspondence between at least one of the attributes corresponding to the plurality of potential delegates to the criterion of interest;

determining, by the database system, from the set of authorized delegates, a number of candidates available to meet the criterion of interest; and issuing an authorization to at least one of the number of available candidates, the authorization allowing the at least one of the number of available candidates to review the subset of private data of the customer and providing a link facilitating login as the at least one of the number of available candidates.

\* \* \* \* \*